United States Patent
Bradbury et al.

(10) Patent No.: US 6,772,026 B2
(45) Date of Patent: Aug. 3, 2004

(54) SYSTEM AND METHOD FOR RAPIDLY CUSTOMIZING DESIGN, MANUFACTURE AND/OR SELECTION OF BIOMEDICAL DEVICES

(75) Inventors: Thomas J. Bradbury, Yardley, PA (US); Christopher M. Gaylo, Princeton Junction, NJ (US); James A. Fairweather, West Haven, CT (US); Kathleen D. Chesmel, Cream Ridge, NJ (US); Peter A. Materna, Metuchen, NJ (US); Adolphe Youssef, Kendall Park, NJ (US)

(73) Assignee: Therics, Inc., Princeton, NJ (US)

( * ) Notice: Subject to any disclaimer, the term of this patent is extended or adjusted under 35 U.S.C. 154(b) by 174 days.

(21) Appl. No.: 09/972,832

(22) Filed: Oct. 5, 2001

(65) Prior Publication Data

US 2002/0059049 A1 May 16, 2002

Related U.S. Application Data

(63) Continuation-in-part of application No. 09/828,504, filed on Apr. 5, 2001
(60) Provisional application No. 60/194,965, filed on Apr. 5, 2000.

(51) Int. Cl.$^7$ .............................................. G06F 19/00
(52) U.S. Cl. ........................... 700/98; 700/97; 700/182; 607/1
(58) Field of Search ............................ 700/98, 97, 119, 700/127, 163, 182

(56) References Cited

U.S. PATENT DOCUMENTS

| | | | |
|---|---|---|---|
| 4,704,686 A | * | 11/1987 | Aldinger ...................... 700/163 |
| 4,822,365 A | * | 4/1989 | Walker et al. .............. 128/898 |
| 4,936,862 A | * | 6/1990 | Walker et al. .............. 128/898 |

(List continued on next page.)

FOREIGN PATENT DOCUMENTS

| | | |
|---|---|---|
| DE | 197 24 724 A1 | 12/1998 |
| EP | 0 097 001 A1 | 12/1983 |
| EP | 0 129 531 A2 | 12/1984 |

(List continued on next page.)

OTHER PUBLICATIONS

Web Page: "Volume Visualization With Ray Casting"—John Pawasauskas Feb 18, 1997.*
Steidle, C., et al., "Automated Fabrication of Custom Bone Implants Using Rapid Prototyping," in *Proceedings of the 44$^{th}$ Int'l SAMPE Symposium and Exhibition*, Long Beach, CA, May 1999.

(List continued on next page.)

*Primary Examiner*—Leo Picard
*Assistant Examiner*—Michael D. Masinick
(74) *Attorney, Agent, or Firm*—Seed IP Law Group PLLC

(57) ABSTRACT

The rapid design and manufacture of biomedical devices such as implants, oral dosage pills and implantable pharmaceuticals employs electronic data and modeling transmissions via a computer network. Patient information and patient-specific radiological data is captured and transmitted via a computer network to a design and/or manufacturing site. A multi-dimensional digital model is created based on the radiological data and patient information. Communications interchanges between a clinical/diagnostic site and a design/manufacturing site permit modification of the digital model until approved. The approved digital model is converted into machine instructions to construct the biomedical device. Alternatively, the digital model is employed in a best fit selection of a biomedical device from a pre-existing set of biomedical devices or machine-instructions. Transmittal of data over computer networks is further directed to the use of a Website to perform various client-interaction and follow-up tasks.

5 Claims, 17 Drawing Sheets

U.S. PATENT DOCUMENTS

| | | | |
|---|---|---|---|
| 5,314,457 A | 5/1994 | Jeutter et al. | 607/116 |
| 5,340,656 A | 8/1994 | Sachs et al. | 428/546 |
| 5,360,446 A | 11/1994 | Kennedy | 623/16 |
| 5,370,692 A | 12/1994 | Fink et al. | 623/16 |
| 5,434,611 A | 7/1995 | Tamura | 348/8 |
| 5,441,047 A | 8/1995 | David et al. | 128/670 |
| 5,448,489 A * | 9/1995 | Reuben | 700/163 |
| 5,449,754 A | 9/1995 | Nishioka | 530/334 |
| 5,452,219 A * | 9/1995 | Dehoff et al. | 700/163 |
| 5,490,962 A * | 2/1996 | Cima et al. | 264/401 |
| 5,503,149 A * | 4/1996 | Beavin | 600/411 |
| 5,580,699 A | 12/1996 | Layman et al. | 430/311 |
| 5,594,651 A | 1/1997 | St. Ville | 364/468.04 |
| 5,595,703 A | 1/1997 | Swaelens et al. | 264/401 |
| 5,655,084 A | 8/1997 | Pinsky et al. | 395/203 |
| 5,658,709 A | 8/1997 | Layman et al. | 430/311 |
| 5,701,904 A | 12/1997 | Simmons et al. | 128/670 |
| 5,715,451 A | 2/1998 | Marlin | 395/615 |
| 5,715,823 A * | 2/1998 | Wood et al. | 600/437 |
| 5,717,769 A | 2/1998 | Williams | 381/67 |
| 5,728,134 A | 3/1998 | Barak | 606/214 |
| 5,732,074 A | 3/1998 | Spaur et al. | 370/313 |
| 5,749,902 A | 5/1998 | Olson et al. | 607/5 |
| 5,749,921 A | 5/1998 | Lenker et al. | 623/1 |
| 5,758,652 A | 6/1998 | Nikolic | 128/673 |
| 5,768,134 A * | 6/1998 | Swaelens et al. | 700/121 |
| 5,769,882 A | 6/1998 | Fogarty et al. | 623/1 |
| 5,772,586 A | 6/1998 | Heinonen et al. | 600/300 |
| 5,773,230 A | 6/1998 | Cheever et al. | 435/7.23 |
| 5,784,635 A | 7/1998 | McCallum | 395/800.32 |
| 5,786,197 A | 7/1998 | Lonetto | 435/220 |
| 5,810,747 A | 9/1998 | Brudny et al. | 600/595 |
| 5,814,161 A | 9/1998 | Sachs et al. | 134/21 |
| 5,815,154 A | 9/1998 | Hirschtick et al. | 345/356 |
| 5,817,110 A | 10/1998 | Kronner | 606/148 |
| 5,824,040 A | 10/1998 | Cox et al. | 623/1 |
| 5,839,438 A | 11/1998 | Graettinger et al. | 128/630 |
| 5,840,020 A | 11/1998 | Heinonen et al. | 600/309 |
| 5,843,005 A | 12/1998 | Chubinsky | 601/15 |
| 5,843,158 A | 12/1998 | Lenker et al. | 623/1 |
| 5,844,995 A | 12/1998 | Williams | 381/67 |
| 5,851,186 A | 12/1998 | Wood et al. | 600/437 |
| 5,862,202 A | 1/1999 | Bashoura et al. | 379/100.14 |
| 5,864,337 A | 1/1999 | Marvin | 345/338 |
| 5,884,246 A | 3/1999 | Boucher et al. | 704/2 |
| 5,890,129 A | 3/1999 | Spurgeon | 705/4 |
| 5,891,035 A | 4/1999 | Wood et al. | 600/437 |
| 5,892,900 A * | 4/1999 | Ginter et al. | 713/200 |
| 5,907,845 A | 5/1999 | Cox et al. | 707/102 |
| 5,911,992 A | 6/1999 | Braswell et al. | 424/195.1 |
| 5,912,720 A | 6/1999 | Berger et al. | 351/206 |
| 5,931,901 A | 8/1999 | Wolfe et al. | 709/206 |
| 5,933,881 A | 8/1999 | Smith | 4/420.4 |
| 5,935,060 A | 8/1999 | Iliff | 600/300 |
| 5,938,737 A | 8/1999 | Smallcomb et al. | 709/247 |
| 5,943,423 A | 8/1999 | Muftic | 380/25 |
| 5,951,300 A | 9/1999 | Brown | 434/236 |
| 5,951,598 A | 9/1999 | Bishay et al. | 607/142 |
| 5,956,687 A | 9/1999 | Wamsley et al. | 705/1 |
| 5,966,126 A | 10/1999 | Szabo | 345/348 |
| 5,966,711 A | 10/1999 | Adams | 707/104 |
| 5,967,986 A | 10/1999 | Cimochowski et al. | 600/454 |
| 5,970,499 A | 10/1999 | Smith et al. | 707/104 |
| 5,972,344 A | 10/1999 | Edwards | 424/195.1 |
| 5,974,124 A | 10/1999 | Schlueter, Jr. et al. | 379/106.02 |
| 5,986,662 A | 11/1999 | Argiro et al. | 345/424 |
| 5,987,519 A | 11/1999 | Peifer et al. | 709/230 |
| 5,989,559 A | 11/1999 | Edwards | 424/195.1 |
| 5,991,731 A | 11/1999 | Colon et al. | 705/3 |
| 5,991,751 A | 11/1999 | Rivette et al. | 707/1 |
| 5,993,001 A | 11/1999 | Bursell et al. | 351/212 |
| 5,995,939 A | 11/1999 | Berman et al. | 705/3 |
| 6,007,459 A | 12/1999 | Burgess | 482/4 |
| 6,009,212 A | 12/1999 | Miller et al. | 382/294 |
| 6,013,260 A | 1/2000 | Edwards | 424/195.1 |
| 6,016,486 A | 1/2000 | Nichols | 706/47 |
| 6,018,731 A | 1/2000 | Bertrand et al. | 706/47 |
| 6,022,315 A | 2/2000 | Iliff | 600/300 |
| 6,022,526 A | 2/2000 | Woodburn et al. | 424/9.61 |
| 6,024,700 A | 2/2000 | Nemirovski et al. | 600/300 |
| 6,027,217 A | 2/2000 | McClure et al. | 351/224 |
| 6,029,159 A | 2/2000 | Zorba et al. | 706/47 |
| 6,125,352 A | 9/2000 | Franklin et al. | 705/26 |
| 6,125,652 A | 10/2000 | Vogel et al. | 62/509 |
| 6,131,087 A | 10/2000 | Luke et al. | 705/26 |
| 6,182,897 B1 | 2/2001 | Knowles et al. | 235/462.01 |
| 2002/0007294 A1 | 1/2002 | Bradbury et al. | 705/7 |
| 2002/0103505 A1 * | 8/2002 | Thompson | 607/1 |

FOREIGN PATENT DOCUMENTS

| | | |
|---|---|---|
| EP | 0 574 098 A1 | 12/1993 |
| EP | 0 668 062 A1 | 8/1995 |
| EP | 0 838 286 A1 | 4/1998 |
| EP | 0 844 581 A2 | 5/1998 |
| WO | WO 95/07509 | 3/1995 |
| WO | WO 97/30652 | 8/1997 |
| WO | WO 99/25396 | 5/1999 |
| WO | WO 01/15058 A1 | 3/2001 |
| WO | WO 01/56654 A1 | 8/2001 |
| WO | WO 01/77988 A2 | 10/2001 |
| WO | WO 01/80761 A2 | 11/2001 |
| WO | WO 03/006107 A1 | 1/2003 |

OTHER PUBLICATIONS

"Dental Implants Frequently Asked Questions," Retrieved Mar. 1, 2000, from <URL: http://www.sfii.com/faqs.htm>.

"Nonresorbable Bone Implants via LOM," Retrieved Mar. 1, 2000, from <URL: http://www.udri.udayton.edu/rpdl/bone-.htm>.

"Biomaterials Laboratory," Retrieved Mar. 1, 2000, from <URL: http://www.uky.edu/RGS/CBME/bmat.html>.

Beumer, J., "Implants in Partially Edentulous Patients; The UCLA Experience," Retrieved Mar. 1, 2000, from <URL: http://www.dent.ucla.edu/pic/visitors/implants/07.html>.

Duke, D., "Radiologist Reaching Rural America Through Improved Technology," Retrieved Mar. 1, 2000, from <URL: http://wupa.wustl.edu/nai/feature/1996/Feb96–Teleradiology.html>.

"Interactive Real–Time Ultrasound Telediagnosis," Retrieved Mar. 1, 2000, from <URL: http://www.telesonography.com/TechnicalPrimer.html>.

Tobin, M., "Teleradiology—A Personal View," Retrieved Mar. 1, 2000, from <URL: http://www.octet.com/~mikety/Articles/PC–Teleradiology/Teleradiology.html>.

"Frequently Asked Teleradiology Questions," Retrieved Mar. 1, 2000, from<URL: http://cter.eng.uab.edu/telemed/faqtrad.html>.

"Software for Establishing Teleradiologic Links for Quantitative Volumetric Imaging Consultation," Retrieved Mar. 1, 2000, from <URL: http://everest.radiology.uiowa.edu/nlm/consult/consult.html>.

Whitehead et al., "Quantitative and Qualitative Light Microscopy of Bone Remodeling at the Interface with Implanted Biomaterials," Retrieved Mar. 1, 2000, from <URL: http://sbec.abe.msstate.edu/abstracts/whitehead.htm>.

"Bone Implant Technologies," Retrieved Mar. 1, 2000, from <URL: http://www.pittsburgh–tissue.net/brochure/Research/NASAbone.html>.

Excerpts from the Introductory Chapter of "Handbook of Teleradiology Applications," Retrieved Mar. 1, 2000, from <URL: http://www.rsna.org/REG/learnres/excerpts.html>.

"Teleradiology Questions and Answers," Retrieved Mar. 1, 2000, from <URL: http://www.mayo.edu/physician/mmi/faq.html>.

Huang, H.K., "PACS: Basic Principles and Applications," Retrieved Aug. 21, 2002, from <URL: http://www.amazon.com/exec/obidos/tg/detail/–/0471253936/qid=1029956152/sr=8–14/ref=sr_8_14/102–1690425–9399327?s=books&n=507846>.

"IntraCom Family of Products Receives FDA Clearance," Retrieved Mar. 1, 2000, from <URL: http://www.intracom.net/news/990217.html>.

Kincade, K., "Teleradiology: Market Opportunity or Predatory Strategy?," Retrieved Mar. 1, 2000, from <URL: http://www.telemedmag.com/topics/clin3.htm>.

Harris, G., "Annual Survey—Teleradiology Service Providers," Retrieved on Feb. 29, 2000, from <URL: http://www-.telemedtoday.com/annnual_survey.htm>.

"Jan. 2000: New Software Release,": Retrieved Mar. 1, 2000, from <URL: http://www.materialise.com/Home.htm>.

"Medical Services," Retrieved Mar. 1, 2000, from <URL: http://www.materialise.com/medical/MedHome.htm>.

"CT–Based Anatomical Modeling: patient–specific pre–surgical planning models," Medical Modeling Corporation, Golden, Colorado, 1999.

$17^{th}$ Symposium for Computer Application in Radiology, "The Electronic Practice: Radiology and the Enterprise," Retrieved on Mar. 1, 2000, from <URL: http://www.scar-.rad.washington.edu/SCAR/meeting2000/2000main.html>.

* cited by examiner-

Assembly Name =Build-010822-A.SLDASM
Date Saved =8/23/2001 4:37:39 PM
Operator =adolphey
Time and Date of Scan =Thu Aug 23 16:47:36 2001
Maximun Assembly Dimensions =0, 0, 0 by 4.3, 25.8, 2.4
Bodies in Assy =Method Bar-2100-2C-1, 01015-XX-3, Method Bar-2100-3-1
Scan Parameters = 0.200000 StartX, 0.100000 StartZ, 20.000000 EndX,
30.000000 EndZ, 0.400000 XIncrement, 0.200000 ZIncrement
Stagger Parameters =0%, 50%
0.2, 0, 0.1, 0, -1, 0, Method Bar-2100-2C-1, FACE ENTER
0.2, 25.8, 0.1, 0, 1, 0, Method Bar-2100-2C-1, FACE EXIT
0.6, 0, 0.1, 0, -1, 0, Method Bar-2100-2C-1, FACE ENTER
0.6, 25.8, 0.1, 0, 1, 0, Method Bar-2100-2C-1, FACE EXIT
1, 0, 0.1, 0, -1, 0, Method Bar-2100-2C-1, FACE ENTER
1, 25.8, 0.1, 0, 1, 0, Method Bar-2100-2C-1, FACE EXIT
1.4, 0, 0.1, 0, -1, 0, Method Bar-2100-2C-1, FACE ENTER
1.4, 25.8, 0.1, 0, 1, 0, Method Bar-2100-2C-1, FACE EXIT
1.8, 0, 0.1, 0, -1, 0, Method Bar-2100-2C-1, FACE ENTER
1.8, 25.8, 0.1, 0, 1, 0, Method Bar-2100-2C-1, FACE EXIT
2.2, 0, 0.1, 0, -1, 0, Method Bar-2100-2C-1, FACE ENTER
2.2, 25.8, 0.1, 0, 1, 0, Method Bar-2100-2C-1, FACE EXIT
2.6, 0, 0.1, 0, -1, 0, Method Bar-2100-2C-1, FACE ENTER
2.6, 25.8, 0.1, 0, 1, 0, Method Bar-2100-2C-1, FACE EXIT
3, 0, 0.1, 0, -1, 0, Method Bar-2100-2C-1, FACE ENTER
3, 25.8, 0.1, 0, 1, 0, Method Bar-2100-2C-1, FACE EXIT
3.4, 0, 0.1, 0, -1, 0, Method Bar-2100-2C-1, FACE ENTER
3.4, 25.8, 0.1, 0, 1, 0, Method Bar-2100-2C-1, FACE EXIT
3.8, 0, 0.1, 0, -1, 0, Method Bar-2100-2C-1, FACE ENTER
3.8, 25.8, 0.1, 0, 1, 0, Method Bar-2100-2C-1, FACE EXIT
4.2, 0, 0.1, 0, -1, 0, Method Bar-2100-2C-1, FACE ENTER
4.2, 25.8, 0.1, 0, 1, 0, Method Bar-2100-2C-1, FACE EXIT
6.6, 20, 0.1, 0, -1, 0, Method Bar-2100-3-1, FACE ENTER
6.6, 24, 0.1, 0, 1, 0, Method Bar-2100-3-1, FACE EXIT
7, 20, 0.1, 0, -1, 0, Method Bar-2100-3-1, FACE ENTER
7, 24, 0.1, 0, 1, 0, Method Bar-2100-3-1, FACE EXIT
7.4, 20, 0.1, 0, -1, 0, Method Bar-2100-3-1, FACE ENTER
7.4, 24, 0.1, 0, 1, 0, Method Bar-2100-3-1, FACE EXIT
7.8, 20, 0.1, 0, -1, 0, Method Bar-2100-3-1, FACE ENTER
7.8, 24, 0.1, 0, 1, 0, Method Bar-2100-3-1, FACE EXIT
8.2, 20, 0.1, 0, -1, 0, Method Bar-2100-3-1, FACE ENTER
8.2, 24, 0.1, 0, 1, 0, Method Bar-2100-3-1, FACE EXIT
8.6, 20, 0.1, 0, -1, 0, Method Bar-2100-3-1, FACE ENTER

*Fig. 11A*

```
8.2, 24, 0.1, 0, 1, 0, Method Bar-2100-3-1, FACE EXIT
8.6, 20, 0.1, 0, -1, 0, Method Bar-2100-3-1, FACE ENTER
8.6, 24, 0.1, 0, 1, 0, Method Bar-2100-3-1, FACE EXIT
9, 0.845111, 0.1, -0.0114296, -0.246522, -0.96907, 01015-XX-3, FACE ENTER
9, 0.854743, 0.1, 0, 0, 0, 01015-XX-3, EDGE ENTER
9, 2.7828, 0.1, 0.00670346, 0.0829407, -0.996532, 01015-XX-3, FACE EXIT
9, 20, 0.1, 0, -1, 0, Method Bar-2100-3-1, FACE ENTER
9, 24, 0.1, 0, 1, 0, Method Bar-2100-3-1, FACE EXIT
9.4, 0.828896, 0.1, -0.00867246, -0.248466, -0.968602, 01015-XX-3, FACE ENTER
9.4, 2.75248, 0.1, 0.00599263, 0.0863596, -0.996246, 01015-XX-3, FACE EXIT
9.8, 0.817056, 0.1, -0.00604873, -0.247557, -0.968855, 01015-XX-3, FACE ENTER
9.8, 2.72834, 0.1, 0.00442224, 0.088391, -0.996076, 01015-XX-3, FACE EXIT
10.2, 0.809263, 0.1, -0.00355619, -0.243509, -0.969892, 01015-XX-3, FACE ENTER
10.2, 2.71349, 0.1, 0.00203793, 0.089001, -0.996029, 01015-XX-3, FACE EXIT
10.6, 0.805295, 0.1, -0.00131688, -0.23607, -0.971735, 01015-XX-3, FACE ENTER
10.6, 2.71108, 0.1, -0.00107933, 0.0884352, -0.996081, 01015-XX-3, FACE EXIT
11, 0.804436, 0.1, 0.000183978, -0.225878, -0.974156, 01015-XX-3, FACE ENTER
11, 2.72424, 0.1, -0.00475605, 0.0872578, -0.996174, 01015-XX-3, FACE EXIT
11.4, 0.805552, 0.1, 0.000909897, -0.21445, -0.976735, 01015-XX-3, FACE ENTER
11.4, 2.75322, 0.1, -0.00747904, 0.0860076, -0.996266, 01015-XX-3, FACE EXIT
11.8, 0.807375, 0.1, 0.000865401, -0.203354, -0.979105, 01015-XX-3, FACE ENTER
11.8, 2.79098, 0.1, -0.00840592, 0.0854495, -0.996307, 01015-XX-3, FACE EXIT
12.2, 0.808429, 0.1, 6.0855e-005, -0.194035, -0.980995, 01015-XX-3, FACE ENTER
12.2, 2.82933, 0.1, -0.0077601, 0.0858339, -0.996279, 01015-XX-3, FACE EXIT
```

*Fig. 11B*

| Instruction | Data |
|---|---|
| 1 | 464 |
| 2 | 150000 |
| 3 | 5000 |
| 4 | -1273 |
| 5 | 125000 |
| 6 | 112 |
| 7 | 800 |
| N | 1 |
| M | 464 |
| O | 1 |
| M | 464 |
| N | 2 |
| P | 0 |
| F | 14 |
| N | 2 |
| P | 0 |
| F | 48 |
| P | 1 |
| F | 11 |
| P | 0 |
| F | 83 |
| P | 0 |
| F | 6 |
| O | 2 |

*Fig. 12A*

| | |
|---|---:|
| P | 0 |
| F | 13 |
| D | 464 |
| P | 0 |
| G | 13 |
| N | 2 |
| P | 0 |
| G | 6 |
| P | 0 |
| G | 79 |
| P | 1 |
| G | 17 |
| P | 0 |
| G | 46 |
| O | 2 |
| P | 0 |
| G | 14 |
| D | 464 |
| P | 0 |
| F | 14 |
| N | 2 |
| P | 0 |
| F | 44 |
| P | 1 |

*Fig. 12B*

SYSTEM AND METHOD FOR RAPIDLY CUSTOMIZING DESIGN, MANUFACTURE AND/OR SELECTION OF BIOMEDICAL DEVICES

CROSS-REFERENCE TO RELATED APPLICATIONS

This application is a continuation-in-part of U.S. application Ser. No. 09/828,504, filed Apr. 5, 2001, currently pending, which in turn claimed the benefit of Provisional Application No. 60/194,965, filed on Apr. 5, 2000, each of which is incorporated herein by reference in its entirety.

TECHNICAL FIELD

The present invention relates generally to the design, manufacture and/or selection of biomedical devices, such as implants, drug delivery devices and/or oral dosages, and more particularly, methods and systems for rapid customization of biomedical devices using computing systems and information networks such as the Internet.

BACKGROUND OF THE INVENTION

A large variety of systems and methods are known for networking computing systems. For example, the World Wide Web ("the Web") provides an interactive computer environment allowing the exchange of information. The Web uses a collection of common protocols and file formats, including the Hypertext Transfer Protocol ("HTTP"), Hypertext Markup Language ("HTML"), SOAP (Simple Object Access Protocol), and XML (extensible Markup Language), to enable users to obtain or exchange information from virtually anywhere in the world, via the Internet. To establish a presence on the Web, organizations construct a "Web site" which generally includes a collection of documents written in a markup language that is accessible by users using an address on the Web, called a Universal Resource Locator ("URL"). Various other networks, such as intranets and/or extranets are also being used as a channel for transmitting information.

Communications networks have proven to be useful for transmitting information for medical applications. Telemedicine typically includes transmitting simple data, remotely monitoring patients' conditions, transmitting visual information, and even transmitting instructions to remotely operate surgical instruments or medical equipment or to provide other medical instructions in real time. Transmission of visual information is typically for diagnostics purposes, allowing medical conditions to be interpreted by specialists at a distant sites, such as is taught in U.S. Pat. Nos. 6,027,217 and 5,655,084.

Surgery often requires material to replace, repair or augment an anatomical body part. For example, a surgeon may employ materials such as autograft or allograft bone or other implants made from metal, plastic, ceramics or other materials. Proper dimensioning of the material, in both shape and size is important. Ill-fitting implants may be less secure, fail to bond at the mating site, or require replacement. Additionally, cosmetic considerations may be a concern depending on the location of the implant.

In practice, a surgeon may prepare several different sizes of replacement material prior to the operation, selecting the best fitting piece during the operation. The material may be manufactured using conventional manufacturing techniques, such as machining and/or molding. Often the best fitting piece still provides a less than satisfactory fit for medical purposes. Customization of the replacement material is often left solely up to the surgeon, requiring the surgeon to adjust the shape of the material during surgery, for example, by grinding off or removing material from implants or adding filler material such as hydroxyapatite powder. Customizing the implant during the surgery lengthens the surgery, and leads to inconsistent quality, which is dependent on the surgeon's sculpting skills.

Surgeons may use physical models or prototypes of patient anatomy prior to surgery to help visualize and prepare for the actual procedure. These prototypes typically employ low cost manufacturing techniques, such as molding. Thus, these prototypes are not of a sufficiently high quality to be used in the body, and are generally limited with respect to the variety and types of materials used. Due to manufacturing and other constraints these prototypes omit structures that are desirable in implants, but that are not necessary to the prototype's intended use in visualization. Thus, these prototypes or physical models are useful only for extra-surgical purposes, such as visualization, practice, planning, and design of templates, and are not intended for use in the body.

SUMMARY OF THE INVENTION

Aspects of the present invention provide a method and system of rapid design, manufacture and/or selection of biomedical devices such as implants, oral dosage pills and implantable pharmaceuticals using electronic data and modeling transmissions via computer networks such as the Internet, intranets and/or extranets. Patient information and patient-specific radiological data may be captured and transmitted via a computer network to a design and/or manufacturing site. A multi-dimensional digital model may be created based on the radiological data and patient information. Communications interchanges between a clinical/diagnostic site and a design/manufacturing site permit modification of the digital model until approved. The approved digital model may be converted into machine instructions to construct the biomedical device. Alternatively, the digital model may be employed in a best fit selection a biomedical device from a pre-existing set biomedical devices or pre-existing set of machine-instructions. Transmittal of data over computer networks may be further directed to the use of a Website to perform various client-interaction and follow-up tasks.

One method for rapid construction of biomedical devices may be three dimensional printing. Such technology allows the manufacture of biomedical devices with a great degree of design freedom and complexity as far as dimensional design, and also as far as material composition, porosity, internal architecture, and the like, taking advantage of the information in the digital models. In particular, it may be possible to design active content into the architecture of the implant, such as drugs, DNA, growth factors, comb polymers, and the like, that can direct, promote, or discourage ingrowth of bone, soft tissues, or vascularized tissue in particular places.

Aspects of the invention may increase the responsiveness of the biomedical device preparation and surgical planning process as well as allowing customized construction of the biomedical device. In some aspects, it may be possible to interchange data to design and dimension a biomedical device, to visualize and confirm its suitability, to manufacture it, to deliver the biomedical device to the physician and implant or use the biomedical device in a patient, all within a few days. An increase in responsiveness will have attendant benefits to patient treatment, especially emergency treatment. It may also reduce geographical restrictions on the availability of medical technology.

In a further aspect, rapid design and/or manufacture of custom pharmaceuticals or drugs such as Oral Dosage Forms (ODF); short-run applications to meet small, acute or emergency needs; or individually designed implantable pharmaceuticals or biomedical devices, may be carried out via transmission of data over computer networks.

BRIEF DESCRIPTION OF THE DRAWINGS

FIGS. 11A and 11B is a program listing showing a set of computer-readable instructions defining header information, intersection points, and type of intersection resulting from a ray casting operation performed on the digital model of FIG. 10.

FIGS. 12A and 12B is a program listing showing a set of computer-readable instructions for driving a three dimensional printer to create a physical copy of the digital model of FIG. 10.

DETAILED DESCRIPTION OF THE INVENTION

In the following description, certain specific details are set forth in order to provide a thorough understanding of various embodiments of the invention. However, one skilled in the art will understand that the invention may be practiced without these details. In other instances, well-known structures associated with computers, computer networks, data structures, databases and networks such as intranets, extranets and the Internet, have not been described in detail to avoid unnecessarily obscuring the descriptions of the embodiments of the invention.

Unless the context requires otherwise, throughout the specification and claims which follow, the word "comprise" and variations thereof, such as "comprises" and "comprising" are to be construed in an open, inclusive sense, that is as "including but not limited to."

The present invention is directed to the preparation of rapid-prototyped biomedical devices manufactured or selected using a patient's own diagnostic data. The biomedical devices may take the form of structural implants, drug delivery implants and/or oral dosages. The diagnostic data may take the form of radiological data, such as data resulting from magnetic resonance imaging ("MRI"), computer tomography ("CT"), and/or X-ray. The diagnostic data is typically acquired at a first site, while engineering and/or manufacturing services and equipment are located at a second site, remote with respect to the first site.

Transmittal of the diagnostic data over telecommunication or computer networks can significantly reduce the time required for device preparation, enhance the surgical planning process, as well as allow the custom manufacturing of the biomedical device. Transmittal of multi-dimensional digital models of the biomedical device over telecommunications or computer networks allows the surgeon or others to visualize and confirm the suitability of the biomedical device. In addition to the biomedical device, the digital model may contain surrounding structure and/or tissue to more accurately represent the fit. Transmittal of requests for modification of the biomedical device over telecommunications or computer networks allows the manufacture and delivery of the anatomically accurate biomedical devices to the physician or surgeon, all within a few days, which is much faster than presently possible. This may greatly increase the responsiveness of the medical practice, with attendant benefits to patient treatment, especially in emergency treatment. It also reduces geographical restrictions on the availability of this medical technology, and can allow the centralization or pooling of resources, such as engineering talent and machine tools.

Figure 1:
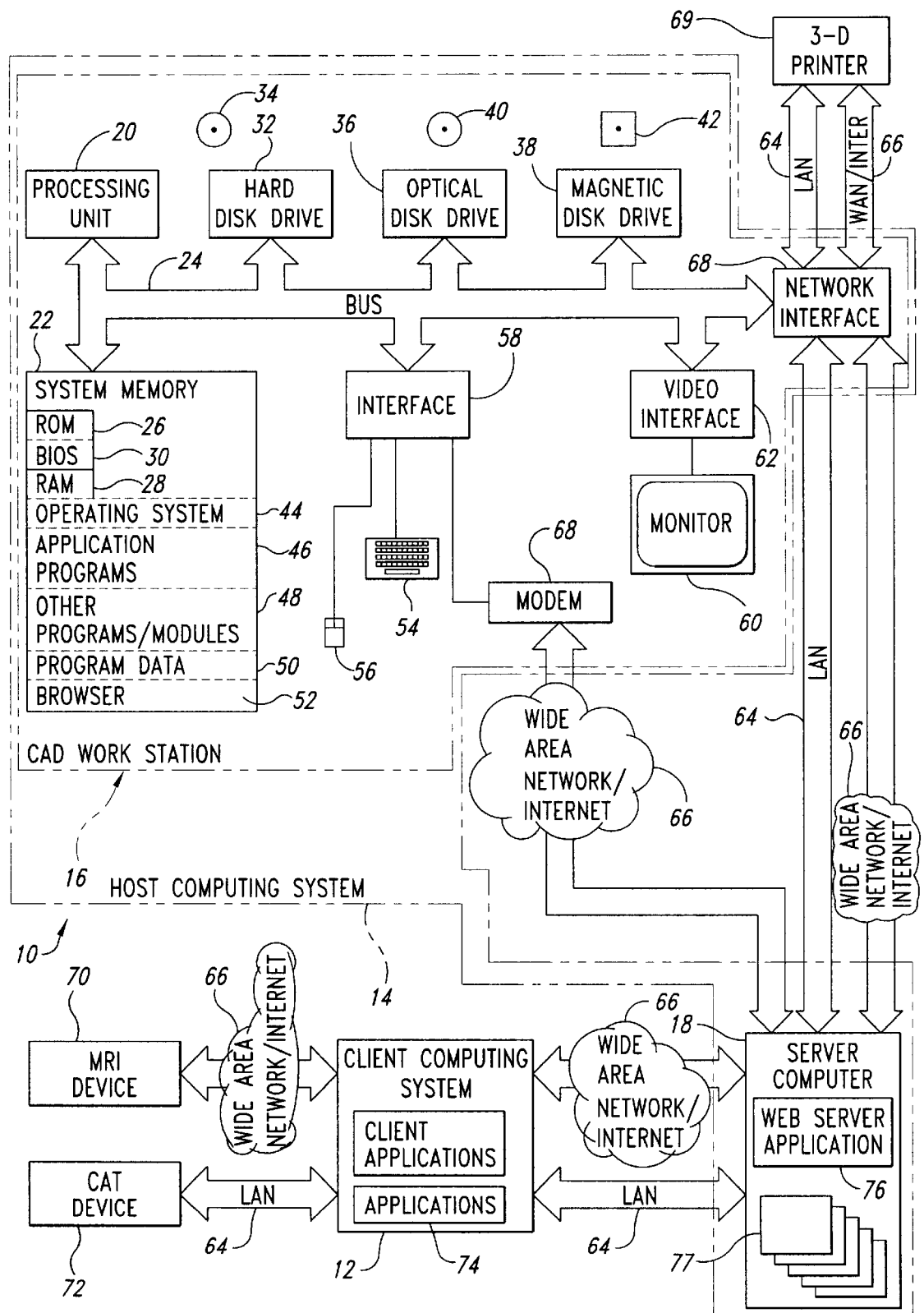
FIG. 1 is a schematic diagram of a biomedical device design, manufacturing and/or selection system including a client computing system and a host computing system having a server computer and a CAD workstation.

FIG. 1 and the following discussion provide a brief, general description of a suitable computing environment in which embodiments of the invention can be implemented. Although not required, embodiments of the invention will be described in the general context of computer-executable instructions, such as program application modules, objects, or macros being executed by a computer. Those skilled in the relevant art will appreciate that the invention can be practiced with other computer system configurations, including hand-held devices, multiprocessor systems, microprocessor-based or programmable consumer electronics, personal computers ("PCs"), network PCs, mini computers, mainframe computers, and the like. The invention can be practiced in distributed computing environments where tasks or modules are performed by remote processing devices, which are linked through a communications network. In a distributed computing environment, program modules may be located in both local and remote memory storage devices.

Referring to FIG. 1, a biomedical device design and manufacturing system includes a client computing system 12 and a host computing system 14. The client computing system 12 may be located at a diagnostic site, such as a hospital, clinic, laboratory or doctor's office. The host computing system 14 may be located at a site remote from the diagnostic site, such as at a site of a biomedical device designer or manufacturer.

The host computing system 14 includes a conventional mainframe or minicomputer, referred to herein as the computer aided design ("CAD") workstation 16 and a server computer 18. While shown as separate devices, the server functionality can be implemented within the CAD workstation 16, which may reduce the cost of the system 10, but may also cause an unacceptable degradation in system performance.

The CAD workstation 16 includes a processing unit 20, a system memory 22 and a system bus 24 that couples various system components including the system memory 22 to the processing unit 20. The CAD workstation 16 and/or server computer 18, will at times be referred to in the singular herein, but this is not intended to limit the application of the invention to a single CAD workstation 16 and/or server computer 18 since in typical embodiments, there will be more than one CAD workstation 16 and/or server computer 18.

The biomedical device design and manufacturing system 10 may employ other computers, such as conventional personal computers, where the size or scale of the system allows. The processing unit 20 may be any logic processing unit, such as one or more central processing units (CPUs), digital signal processors (DSPs), application-specific integrated circuits (ASICs), etc. Unless described otherwise, the construction and operation of the various blocks shown in FIG. 1 are of conventional design. As a result, such blocks need not be described in further detail herein, as they will be understood by those skilled in the relevant art.

The system bus 24 can employ any known bus structures or architectures, including a memory bus with memory controller, a peripheral bus, and a local bus. The system memory 22 includes read-only memory ("ROM") 26 and random access memory ("RAM") 28. A basic input/output system ("BIOS") 30, which can form part of the ROM 26, contains basic routines that help transfer information between elements within the CAD workstation 16, such as during start-up.

The CAD workstation 16 also includes a hard disk drive 32 for reading from and writing to a hard disk 34, and an optical disk drive 36 and a magnetic disk drive 38 for reading from and writing to removable optical disks 40 and magnetic disks 42, respectively. The optical disk 40 can be a CD-ROM, while the magnetic disk 42 can be a magnetic floppy disk or diskette. The hard disk drive 34, optical disk drive 40 and magnetic disk drive 42 communicate with the processing unit 20 via the bus 24. The hard disk drive 32, optical disk drive 36 and magnetic disk drive 38 may include interfaces or controllers (not shown) coupled between such drives and the bus 24, as is known by those skilled in the relevant art. The drives 32, 36 and 38, and their associated computer-readable media 34, 40, 42, provide nonvolatile storage of computer readable instructions, data structures, program modules and other data for the CAD workstation 16. Although the depicted CAD workstation 16 employs hard disk 34, optical disk 40 and magnetic disk 42, those skilled in the relevant art will appreciate that other types of computer-readable media that can store data accessible by a computer may be employed, such as magnetic cassettes, flash memory cards, digital video disks ("DVD"), Bernoulli cartridges, RAMs, ROMs, smart cards, etc.

Program modules can be stored in the system memory 22, such as an operating system 44, one or more application programs 46, other programs or modules 48 and program data 50. The system memory 16 may also include a Web client or browser 52 for permitting the CAD workstation 16 to access and exchange data with sources such as Web sites of the Internet, corporate intranets, or other networks as described below, as well as other server applications on server computers including the server computer 18, such as those further discussed below. The browser 52 in the depicted embodiment is markup language based, such as Hypertext Markup Language (HTML), Extensible Markup Language (XML) or Wireless Markup Language (WML), and operates with markup languages that use syntactically delimited characters added to the data of a document to represent the structure of the document. A number of Web clients or browsers are commercially available such as NETSCAPE NAVIGATOR from America Online, and INTERNET EXPLORER available from Microsoft of Redmond, Wash.

While shown in FIG. 1 as being stored in the system memory 22, the operating system 44, application programs 46, other programs/modules 48, program data 50 and browser 52 can be stored on the hard disk 34 of the hard disk drive 32, the optical disk 40 of the optical disk drive 36, the magnetic disk 42 of the magnetic disk drive 38 and/or other computer-readable media. An operator, such as a mechanical engineer or technician, can enter commands and information into the CAD workstation 16 through input devices such as a keyboard 54 and a pointing device such as a mouse 56. Other input devices can include a microphone, joystick, game pad, scanner, etc. These and other input devices are connected to the processing unit 20 through an interface 58 such as a serial port interface that couples to the bus 24, although other interfaces such as a parallel port, a game port or a wireless interface or a universal serial bus ("USB") can be used. A monitor 60 or other display device is coupled to the bus 24 via a video interface 62, such as a video adapter. The CAD workstation 16 can include other output devices, such as speakers, printers, etc.

The CAD workstation 16 can operate in a networked environment using logical connections to one or more remote computers, such as the server computer 18 and client computing system 12. The server computer 18 can be another personal computer, a server, another type of computer, or a collection of more than one computer communicatively linked together and typically includes many or all of the elements described above for the CAD workstation 16. The server computer 18 is logically connected to one or more of the client computing systems 12 and CAD workstations 16 under any known method of permitting computers to communicate, such as through a local area network ("LAN") 64, or a wide area network ("WAN") or the Internet 66. Such networking environments are well known in wired and wireless enterprise-wide computer networks, intranets, extranets, and the Internet. Other embodiments include other types of communication networks including telecommunications networks, cellular networks, paging networks, and other mobile networks.

When used in a LAN networking environment, the CAD workstation 16 is connected to the LAN 64 through an adapter or network interface 68 (communicatively linked to the bus 24). When used in a WAN networking environment, the CAD workstation 16 may include a modem 68 or other device, such as the network interface 68, for establishing communications over the WAN/Internet 66. The modem 68 is shown in FIG. 1 as communicatively linked between the interface 58 and the WAN/Internet 66. In a networked environment, program modules, application programs, or data, or portions thereof, can be stored on, or passed through, the server computer 18. In the depicted embodiment, the CAD workstation 16 is communicatively linked to the server computer 18 through the LAN 64 or the WAN/Internet 66 with TCP/IP middle layer network protocols; however, other similar network protocol layers are used in other embodiments, such as User Datagram Protocol ("UDP"). Those skilled in the relevant art will readily recognize that the network connections shown in FIG. 1 are only some examples of establishing communication links between computers, and other links may be used, including wireless links.

The host computing system 14 include one or more peripheral devices for producing biomedical devices based on the digital models. For example, host computing system 14 may include a 3-dimensional printer 69 coupled to the CAD workstation 16 to receive machine instructions over the LAN 64 and/or WAN or Internet 66.

The client computing system 14 contains many of the same or similar structures, systems and subsystems as the CAD workstation 16, thus only the differences will be discussed in detail. The client computing system 14 is communicatively linked to a first biomedical sensor, such as an MRI device 70, typically through the LAN 64 or the WAN/Internet 66 or other networking configuration such as a direct asynchronous connection (not shown). The client computing system 14 may also be communicatively linked to a second biomedical sensor, such as a CT device 24, typically through the LAN 64 or the WAN/Internet 66 or other networking configuration such as a direct asynchronous connection (not shown). While not illustrated, the client computing system 14 may include more than one computer, and may include a server (not shown) for networking a number of client computers. The client computing system 14 may include client software applications 73 for resolving, managing or manipulating the diagnostic data from the MRI device 70 and/or CT device 72. The client computing system 14 may include software applications for communicating with the CAD workstation 16, for example, a browser 74. The software applications can be stored on any of a variety of computer-readable media.

The server computer 18 contains many of the same or similar structures, systems and subsystems as the CAD workstation 16, thus only the differences will be discussed in detail. The server computer 18 includes server applications 76 for the routing of instructions, programs, data and agents between the MRI device 70, CT device 72, client computing system 12 and CAD workstation 16. For example the server applications 76 may include conventional server applications such as WINDOWS NT 4.0 Server, and/or WINDOWS 2000 Server, available from Microsoft Corporation of Redmond, Wash. Additionally, or alternatively, the server applications 76 can include any of a number of commercially available Web servers, such as INTERNET INFORMATION SERVICE from Microsoft Corporation and/or IPLANET from Netscape. The server computer 18 also includes one or more secure Webpages 77, serving as a user interface ("UI") for exchanging data, information and requests between the diagnostic and/or clinical sites and the design and/or manufacturing sites. The server applications 76 and/or Webpages 77 can be stored on any of a variety of computer-readable media.

Figure 2A:
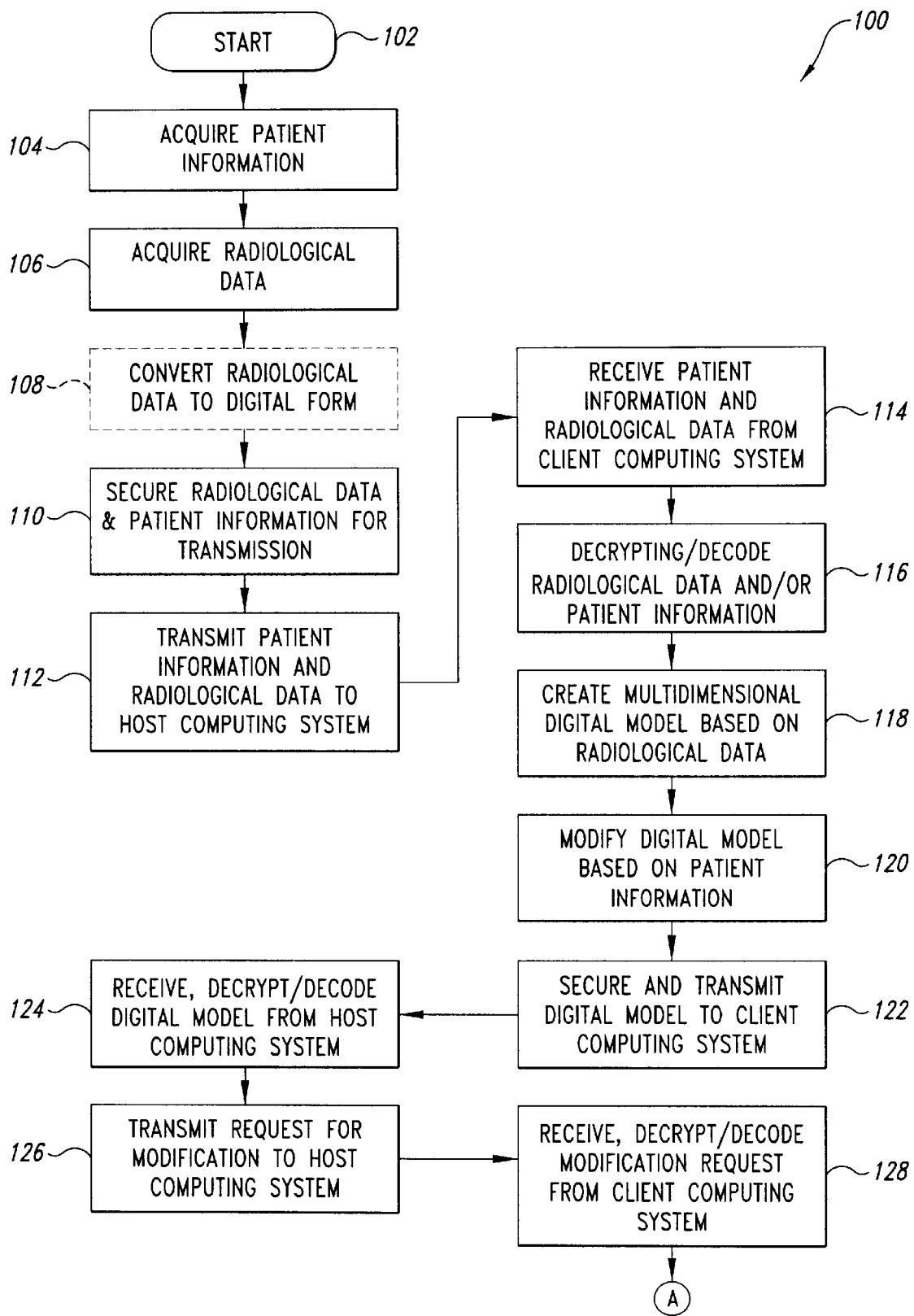
FIGS. 2A and 2B are a flow diagram showing a method of operating the biomedical device design and manufacturing selection system of FIG. 1, for rapid design and delivery of biomedical devices such as implants, dosage implants and/or oral dosages.
Figure 2B:
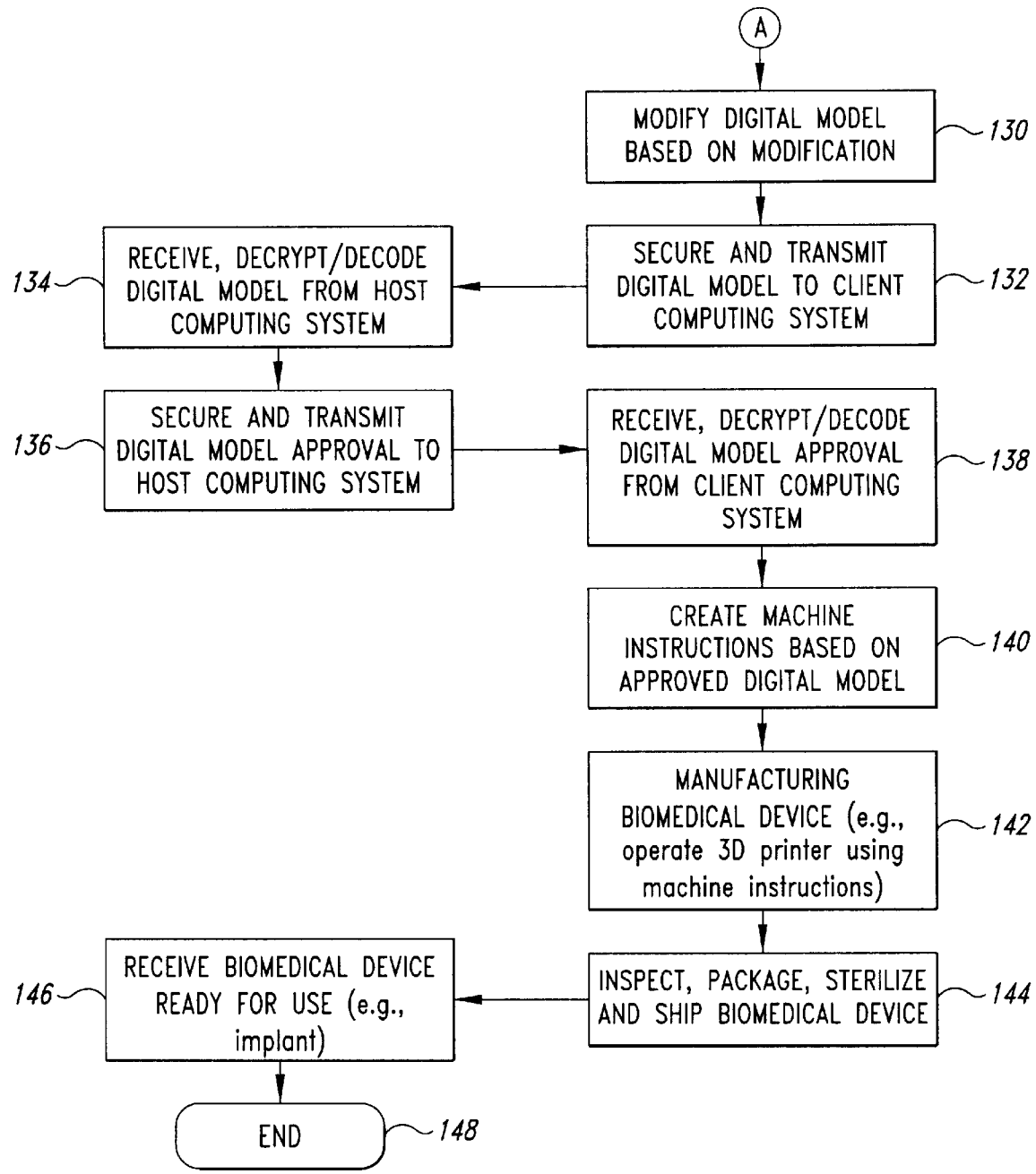

FIGS. 2A and 2B is a flow diagram showing steps of a method 100 in accordance with one embodiment of the present invention, starting in step 102. Steps on the left side of the flow diagram correspond to client side operations, while steps on the right side of the flow diagram correspond to host or server side operations. In step 104, the attending physician or assistant at the diagnostic or clinical site acquires patient information. Patient information can include non-radiological patient data such as a patient's gender, a patient's age, a unique patient identifier, a dosage, allergies, sensitivities to drugs, medical history and/or one or more physical dimensions such as height, weight, length, circumference.

In step 106, the attending physician acquires patient-specific radiological data regarding the surgical or reconstruction site. As discussed generally above and in detail below, radiological data may be acquired using an MRI device 70 (FIG. 1), CT device 72, ultrasound device, nuclear medicine based device, mammography device, or other transducer. The output from the transducer may take a variety of forms, for example, digital or analog electrical signals, or displayed or printed images. In optional step 108, the client computing system 12 converts the acquired radiological data into a suitable form for transmission. For example, the client computing system 12 may convert analog electrical signals into a digital representation suitable for transmission over the communications network, or the client computing system 12 may digitize a printed image. In many embodiments, the transducer output will be in digital form, and thus will not require significant conversion. After conversion, the client computing system 12 may save the radiological data into a computer hard drive, floppy disk, compact disk, or other form of data storage.

In step 110, the client computing system 12 applies any desired security measures to the radiological data and patient information, prior to transmission. Security may be an important feature for protecting patient confidentiality, and may even be required by current or future legislation. For example, the radiological data and patient information can be encrypted, password protected and/or authenticated using digital certificates, such as by conventional public key encryption techniques. In step 112, the client computing system 12 securely transmits the radiological data and patient information to the host computing system 14 using encryption, password protection, digital certificates and/or other methods for providing secure communications.

In step 114, the host computing system 14 receives the transmitted radiological data and patient information at the server 18. In step 116, the host computing system 12 decrypts, decodes and/or otherwise gains access to the radiological data and/or patient information, as required. The server 18 may decrypt and/or decode the radiological data and patient information before forwarding the radiological data and patient information to the CAD workstation 16. Alternatively, the server 18 may forward the encrypted or encoded radiological data and/or patent information to the CAD workstation 16, relying on the CAD workstation 16 to decrypt and/or decode the radiological data and/or patient information.

In step 118, the CAD workstation 16 creates a multi-dimensional digital model from the radiological data. The term digital is employed to clearly distinguish the abstract representation from physical models. The multi-dimensional digital model may take the form of a CAD solid model, surface or wire-frame representation, employing any of a variety of standard CAD formats and commercially available CAD packages, some of which are discussed below.

In step 120, the CAD workstation 16 modifies the multi-dimensional digital model, for example, based on the patient information. For example, the geometry of the multi-dimensional digital model may be modified to add attachment structure, fixture points, separation markings, boundaries or surfaces between various bodily structures and/or other elements not contain in, or difficult to discern from the radiological data. Patient information such as gender, age, weight or height may be used to select certain characteristics using histographic or demographic information. For example, the patient age and/or gender may be used to select an appropriate bone density or porosity from a database of demographic bone density or porosity information. The digital model can be modified to produce an appropriate bone density or porosity, and may even reflect a gradation of bone density or porosity along one or more directions. The host computing system 14 may rely on one or more stored transformations for modifying the digital model. The stored transformations can take the form of predefined scripts for executing one or more CAD functions on the digital model. The transformations may be selected by the operator, or may be automatically selected and applied by the host computing system 14. For example, the host computing system 14 may automatically select and apply a given transformation based on one or more pieces of the patient information.

In step 122, the host computing system 14 encrypts and/or encodes the digital model and transmits the secured digital model to the client computing system 12. In step 124, the client computing system 12 receives the digital model and decrypts and/or decodes the same. The attending physician may view the digital model, for example displaying the model on a display using standard CAD packages or limited functionality viewers for CAD files (i.e., software packages that permit viewing, but not editing). In step 126, the client computing system 12 transmits one or more requests for modification to the host computing system 14. As in the other communications, the requests for modification may be encrypted and/or encoded to secure the communications.

In step 128, the host computing system 14 receives the requests for modification, and decrypts and/or decodes the same. In step 130, the CAD workstation 16 modifies the digital model based on the modification requests. The modification may require the exercise of significant skill by the CAD operator, who may be an engineer or appropriately trained technician. The CAD operator must ensure that the requested modification is implemented in a fashion consistent with the available materials, equipment and manufacturing techniques. This approach reduces or eliminates the need for the physician to understand the details of materials and/or manufacturing. In step 132, the host computing system 14 transmits the modified digital model to the client computing system 12, employing appropriate security measures. In step 134, the client computing system 12 receives, decrypts and/or decodes the modified digital model. The steps 124–134 can be repeated until the attending physician is satisfied with the digital model. In step 136, the client computing system 12 transmits an approval to the host computing system, indicating that the attending physician is satisfied with the digital model.

In step 138, the host computing system 14 receives the model approval from the client computing system 12, and decrypts and/or decodes the same, if necessary. In step 140, the CAD workstation 16 creates machine instructions from the digital model. In step 142, the customized biometric device is manufactured using the approved digital model. Manufacture may employ standard computer aided manufacturing ("CAM") techniques such as machining or molding. However, the manufacturing may employ 3-D printing to take advantage of the information inherent in the digital model which is not typically reproducible using standard manufacturing techniques. For example, the digital model may define internal structures, different materials, densities, density gradients, pharmacological agents and the like, which may require 3-D printing to create such structure in a finished product. Various devices made by three-dimensional printing methods were disclosed in U.S. Pat. No. 5,490,962. In step 144, the customized biomedical device is sterilized, packaged and shipped to the physician. In step 146, the physician receives the biomedical device, wherein the anatomically accurate biomedical device such as an implant is ready to be implanted in the patient or otherwise used. The method 100 terminates in step 148.

In manufacturing customized implants or other biomedical devices, the starting point is the patient-specific data (i.e., radiological data, patient information), obtained from various non-invasive or invasive procedures. Typical non-invasive procedures from which radiological data may be obtained include diagnostic or clinical procedures such as magnetic resonance imaging (MRI) scans, computerized tomography (CT) scans, ultrasounds, nuclear medicine procedures or mammography procedures. Additionally, standard radiographs such as x-rays may be digitized into an electronic file by either a video camera or a film scanner. Yet another type of imaging equipment, which may be useful, although only for measuring external contours of the body, is a laser scanner which digitizes the contours of an external surface. Details of how medical images can be stored, transmitted and handled are given in "PACS: Basic Principles and Applications," by H. K Huang (editor), 1999 Liley-Liss, and in the same author's earlier book, "PACS: Picture Archiving and Communication Systems in Biomedical Imaging."

The radiological imaging equipment is available at many medical facilities, but other equipment involved in the present invention is more specialized and may only be available at few centralized locations. This makes it useful to transmit diagnostic imaging information from the patient's location to a central site, allowing global access to otherwise limited design and manufacturing resources.

One example of a framework for transmitting electronic medical imaging data between various sites is the "Digital Imaging Communications in Medicine ("DICOM") standard developed by the American College of Radiology ("ACR") and the National Electrical Manufacturer's Association ("NEMA"). DICOM is based upon the Open System Interconnect (OSI) reference model, which defines a 7-layer protocol. Data may further be transmitted via common telephone lines (twisted pairs of copper wire), digital phone lines (ISDN, switched-56), DSL, coaxial cable, cable modem, fiber-optic cable, microwave, satellite, and T-1, T-3, OC-3, and other forms of telecommunications links. In regard to all data transmissions mentioned herein, privacy and security issues have become prominent issues in regard to the maintenance and transfer of individuals' medical data. Accordingly, it would be advantageous to encrypt the data before transmission and to decrypt the data after transmission, as is known in the art. Alternately, data could also be transmitted, for example, by storing the data on a data storage device such as a floppy disc, compact disc, DVD disc, optical disc, magneto-optic disc, WORM (write once read many times) disc, and sending the storage device via traditional mail services. In the event that the manufacturing site coincides with the location of the patient, the doctor and the diagnostic equipment, data transmission via the Internet may not be necessary.

Radiological data such as MRI or CT scans is normally presented as sets of two-dimensional images (sections) showing all of the patient's tissues. The slices in a CT scan or an MRI scan associate an intensity of brightness on the display with each coordinate location in a scan. In a CT scan, darkness corresponds to absorption of X-rays, that most closely correlates with density of the tissue. In an MRI scan, intensity refers to the presence of certain elements. CT scans are considered better for imaging hard tissue such as bone, and MRI scans are considered better for imaging soft tissue. There may be instances in which it is advantageous to use both types of imaging together with each other.

In some instances, for example, an implant that joins to existing bone, the diagnostic scans may need further processing. Further processing may include, for example, more clearly distinguishing between hard and soft tissue, as well as defining solid boundaries or surfaces of the hard tissue, for example, bone, in the two-dimensional planes or sections in which the MRI or CT scans typically are presented. Identifying the edges or surfaces of bone can be achieved by appropriate sampling and threshold definition techniques (perhaps including contrast enhancement) and geometrical algorithms such as in the software package MIMICS (from Materialise Europe; Ann Arbor, Mich.). This initially processed data may further be converted to a form that geometrically represents a multi-dimensional form representing an object. Such mathematical representations typically feature curved surfaces with resolution available to almost any desired precision anywhere on the surface, not only at locations which were part of the scan planes of the original MRI or CT data. For at least some of the types of radiological data (e.g., MRI or CT scans), there is a coarseness in the raw data that is acquired by radiologists or other medical personnel. Typically data is available at sampling planes which are parallel to each other and are spaced apart at intervals of 1 to 2 millimeters, which is coarser than the feature size typically desired in a custom manufactured implant. This increased or improved level of geometric detail is achieved through, for example, the use of interpolation, curve fitting, spline fitting, and surface fitting.

A solid model is a geometric description of the entire surface of a solid object, where solid portions border empty space, as opposed to a description of the interior or solid region of the object. Solid surfaces are represented by patching together descriptions of individual portions of the surface together with definitions of intersections or regions in which each description applies. The descriptions of individual surface regions can in simple instances be segments of simple geometries such as planes, spheres, cylinders, toroids or other revolved surfaces. More generally the descriptions of individual surface regions can be curved surfaces of varieties such as bilinear surfaces, Coon's patch, bicubic patch, Bezier surfaces, B-spline surfaces, non-uniform rational B-spline ("NURBS") surfaces, interpolation surfaces, and others as are known in the art. Intersections between surfaces can be described as series of intersection points. This information can be stored in file formats such as Initial Graphics Exchange Specifications ("IGES"), which is defined by ANSI Standard Y144.26M, and Standard for the Exchange of Product ("STEP") model data. A more limited type of data transfer is provided by Drawing Interchange Format ("DXF") used for AutoCAD files, and the like. Such models underlie most of the CAD software used for engineering and design of mechanical parts.

Once a digital model has been created from the diagnostic data, the multi-dimensional digital model essentially becomes just another data set or mathematical object capable of being further processed or manipulated by standard CAD software. Suitable CAD software packages for further processing the digital model include SolidWorks (SolidWorks, Concord Mass.) and ProEngineer (Parametric Technologies, Waltham, Mass.).

In accordance with another embodiment, radiological data is combined from more than one type of scan, such as MRI and CT. In combining two different scans typically taken with two different sets of equipment and two different positionings of the patient, one challenge is to determine the appropriate relative position and orientation of the models obtained from the two methods. One approach is to employ the CAD software's ability to calculate the centroid of a solid object. Aligning centroids of objects resulting from different types of scans is one way of comparing them. Alternatively, or in conjunction with aligning the centroids, the parts can be aligned as far as angular orientation. Another approach employs the CAD software's ability to mathematically subtract one model from the other, for example, by a Boolean operation, to obtain a set of space representing points which are members of one model or the other model but not both. The volume is calculated by the CAD software. When the volume of this spatial difference is minimized, the best alignment of the two parts has been achieved. After the best alignment is achieved, a combination or average of the two scan results could be calculated and used for the best representation of the surfaces.

The digital model created so far from diagnostic data may be, for example, a model of existing bone structure in a patient's body. As a first step in creating a model of the object to be manufactured, a decision must be made as to whether the part which is to be manufactured corresponds to solid regions displayed in a diagnostic scan (i.e., if the part is a replacement part), or if it corresponds to voids displayed in a diagnostic scan (i.e., if it is a filler piece). If the part is a replacement part, it is possible that all of its edges are defined by edges of existing bone that is already represented by the digital model. If it is a filler piece, some of its edges can be mathematically defined by Boolean operations in the CAD program where the part adjoins pieces that are already defined as solid (e.g., existing bones). Where the new part adjoins soft tissue, the CAD operator may have to define the edges. A mating bone may be removed or moved to a new position in the digital model.

In alternative embodiments, other auxiliary software such as software that is typically used by plastic and cosmetic surgeons to predict external body appearance may be used. For example, CAD software allows geometric manipulation of an original design of a part such as to add material in certain locations or to remove material in certain locations for reasons of strength, appearance, cosmetic appeal, and the like.

In another embodiment, other features could be added to the digital model, involving either removal or addition of material, such as features that pertain to attachment of the new part to bones or structures such as those already existing in the body. This could be, for examples, a hole for bone screws. An attachment feature may include a cut, protrusion, hole, or specific dimension in a specific region of the biomedical device. Replacement of a portion of or a complete jawbone may require planning not only for the implant of the bone itself into the jaw, but also for later implantation of artificial teeth or endosseous implants into the implant. Yet another modification could include designating dimensional reference points in the implant for use during surgery for locating the intended position of the part with respect to a template or other references, or for measuring dimensions radiologically after implantation.

In yet another embodiment, the same computerized information could be used to manufacture models out of ordinary non-sterile, non-biocompatible materials of the surgical site and/or implants, for purposes of visualization or surgical planning. Creating digital models advantageously allows trying out different surgical approaches, attachment points, final cosmetic fit and the like.

Creating digital models also allows templates, tools or similar related surgical hardware to be designed with the design of the implant. Those related surgical hardware items could then be supplied to the customer together with the implant, either custom made or selected from a range of sizes available from stock. It might be desirable for the surface of the implant to have a surface texture or pattern designed in to the multi-dimensional digital model as a feature not included in the radiological data.

Yet another geometric modification could be changing the digital model, for example, enlarging the entire part by a predetermined factor in all or certain directions to compensate for anticipated shrinkage during post-manufacturing processing steps. Such shrinkage is known in the art, along with how to compensate for it.

The required software and computer facilities may be so sophisticated, expensive and/or specialized at to be unavailable at an individual physician's office. Use of the Internet would provide easy access to such facilities via a central site. The digital model may be stored, processed and transmitted in the form of an IGES, STEP or similar file, as previously described.

Beyond geometric alteration, there is also another possible step of the process of designing a biomedical device such as an implant. This step requires associating a composition variable or an internal architecture with specific geometric locations in the digital model. Composition variation can be implemented in three-dimensional printing, for example, by dispensing various different binder liquids from different dispensers, with coordination of the dispensers so that their relative target points are known. Additionally, specific chemicals in predetermined locations may be seeded into the implant during manufacturing. For example, growth factors, DNA, etc. can encourage ingrowth of bodily tissue such as bone at designated places. Comb polymers can encourage or discourage various types of cells from locating in designated places, as can modifiers of surface hydrophobicity. Porosity of the final product can also be designed in as a variable. Depending on the desired size scale of porosity, it can be designed into the architecture or can be achieved by manufacturing details, as is known in the art. Color, including variations of color, could also be designed in if desired. It would be possible to put in marker substances that show up on MRI or other forms of radiography, so that the part can be easily inspected. For example, two or more markers could be designed in to the part at a known distance apart from each other. Depending on the modeling software, it may be possible to associate these details with the digital model at this stage. If such compositional details are not incorporated into the digital model, they can be incorporated in the machine instruction file.

Other design conveniences are also possible. For example, because the nearby bones and the proposed new part all exist as digital models, it is possible to assemble them to give a complete description of what the final site will look like. CAD software is capable of automatically checking for mechanical interferences and can further assess the assemblability. The assemblability includes, for example, the assembly sequences, geometric tolerances and tolerance stack-up, design clearances, insertion and motion paths for parts as they are moved into place, all of which are directed toward avoiding interferences of ordinary mechanical parts as they are being assembled.

In another embodiment, sections of the digital models can be calculated in orientations that resemble those of the original diagnostic radiographs for purposes of comparison. Thus, the physician and/or patient can view what a CT, MRI, simple X-ray, or other diagnostic should look like after implantation of the proposed part. Software for visualizing the exterior of the human body, such as software used for planning plastic and cosmetic surgery, could further help visualization. The system may incorporate modeling rules for ingrowth of bone or reabsorption of implant material into the body to simulate the time-progression of growth processes after the implant is implanted in the patient. This simulation could be transmitted back to the physician nearly instantaneously.

In yet another embodiment of the present invention, a digital model can be used to create a mesh for finite element analysis, for example, stress distribution due to applied loads. Such analysis, which is linked to the digital model derived from the patient-specific radiological data, could provide patient-unique calculated stress margins with respect to defined loads. Such stress analysis could, for example, be performed at the remote facility providing the modeling services. The stress analysis could be part of the process of consulting with and obtaining approval from the physician.

In one embodiment, the designed digital model data is transmitted back to the physician and/or patient for their review. Multiple review iterations may be performed as changes are discussed and agreement is reached with the doctor/patient. A system 10 that is implemented in hardware could allow a substantial number of design iterations in a short period of time particularly if it operates in near real time. Further, such a system 10 could provide the medical field a capability of concurrent design or collaborative or interactive design. The final digital model file can be transmitted over the Internet to the manufacturing machine if that machine is located at still another location. Thus, the computer facilities and software that process the radiological data to form the digital model do not have to be co-located with the manufacturing facility.

In yet another embodiment, various details are transmitted back to the client or physician for viewing along with the digital model. If the transmittal of proposed designs from the remote location back to the physician is done by files such as IGES or STEP, it will be possible to transmit as much geometric detail as desired, but it may not be possible to transmit much compositional detail such as distributions of color on the surface, or other compositional variation such as placement of bioactive substances. IGES would be more limiting than STEP in this respect. If the transmission of data is done with proprietary file formats, it may require that the physician use a particular CAD software for viewing the image of the proposed part. It may not be necessary for the physician to have a complete license to the CAD software used in making the patient-unique digital model; since many software packages offer simplified versions having the capability of opening and viewing files generated by the program, but without the ability to modify such files. Alternatively, the computer terminal at the physician could simply be configured as a remote user of the software that is installed at the host computing system 14 (FIG. 1).

Encryption, password protection and digital certificate authentication is desirable in any such data transmission. Transmission of approval from the physician to the manufacturer can be stored with the file containing the agreed-upon design, forming a record of the same.

One method of constructing the biomedical devices employs three-dimensional printing. Three-dimensional printing (3DP) involves selectively bonding together powder in successively deposited layers to form generalized solid shapes. Three dimensional printing processes are detailed in U.S. Pat. Nos. 5,204,055, 5,387,380, 5,807,437, 5,340,656, 5,490,882, 5,814,161, 5,490,962, 5,518,680, and 5,869,170, all hereby incorporated by reference. In three-dimensional printing, there are two principal ways of depositing a layer of powder. In some cases a roller spreads a layer of dry powder. In other cases a continuously dispensing jet moving back and forth in a raster pattern until an entire layer is deposited deposits a layer of slurry typically. The latter method is typically used for depositing relatively thin layers of relatively small particle dimension powder, compared to roller spreading. Either method could be used for present purposes depending on requirements for feature size, mechanical strength of the finished part, and other variables as are known in the art. The choice of binder liquid is also of importance and is selected for particular applications as is known in the art. The binder liquid can be dispensed by a drop-on-demand print head, which may be a piezoelectric print head, or a continuous-jet-with-deflection printhead, or others as are known in the art.

Since the intended process is for medical use, the equipment must include certain medical-specific features. For example, the equipment and/or end product may need to be sterile. Furthermore, the use of printing materials, including powder, binder and any subsequent filling, infusing or other processing materials, should be compatible with the human body. Biocompatible substances for all these materials are known in the art.

Since three-dimensional printing involves printing in layers, it requires instructions in which a multi-dimensional digital model is mathematically translated into a series of slices of narrow thickness, each slice having a set of data or printing instructions representing the part geometry at that particular plane. In three-dimensional printing, each slice corresponds to a layer of powder in the powder bed during construction of the object. The entire set of data or instructions is referred to as the machine instructions.

In a general sense, the slices which are the manufacturing instructions bear a general resemblance to the scan planes which make up an MRI scan or CT scan, but there are important differences. The slices in an MRI or CT scan are acquired diagnostic data. The slices that are manufacturing instructions are processed data containing additional information. The slices that are the manufacturing instructions are typically spaced at the layer thickness of powder spreading, rather than at the scan planes interval of MRI or CT. Quite possibly, the powder layer spacing interval is much smaller than the scan plane interval of the MRI or CT. Additionally, the angular orientation at which the manufacturing slices are taken does not need to have any particular orientation with respect to the angular orientation of the scan planes of MRI or CT. The scan planes are for convenience of diagnostic imaging, and the manufacturing slices are for convenience of manufacturing. The slices in a CT scan or an MRI scan associate with each coordinate location in a scan and an intensity of brightness on the display. In the case of a CT scan, darkness corresponds to absorption of X-rays that is most closely correlated with density of the tissue. In an MRI scan, intensity refers to the presence of certain chemical elements. Both of these types of quantities can have a whole range of values (i.e., analog). In contrast, the print instructions for any given coordinate location are in many cases essentially binary, instructing particular dispensers to either dispense or not dispense.

Generating the machine instructions includes mathematically taking a cross-section of the digital model at locations corresponding to the layers of the three-dimensional printing process. The machine instructions describe the entire interior solid structure of the part, whereas the digital model merely describes the surface. Generating the machine instructions for each coordinate point or voxel in the powder array or printing region include determining whether that coordinate point is to be bound powder and therefore part of the solid or is to be left as unbound powder and therefore empty space the final part. A voxel is a unit of graphic or physical modeling information that defines a point in three-dimensional space. For example, in 3-D space, each of the coordinates may be defined in terms of its position, color, and density. Voxels are commonly used as the smallest individually addressable element in medical imaging and three-dimensional printing applications.

The motion of the printhead as it moves along the fast axis can be considered a line or a ray that intersects the digital model. This is especially true for raster printing, in which the motion of the printhead is always along a straight line, as opposed to vector printing, in which the motion of the printhead can be a curved path. That intersection can be mathematically calculated to indicate for each point or printing location along the ray whether that point should have a dispense command or no command. This process is called ray casting, and basically amounts to mathematically calculating intersections between lines and the digital model. For example, each intersection point between the ray and the surface can be characterized as an entry or an exit. If an entry point has already been reached but no exit point has been reached along that ray, then all points on the ray between entry and exit are part of the solid and require dispensing of binder. Special cases can also be recognized for situation such as tangency where a ray touches but does not really enter a solid body. Thus, the machine instructions include instructions to dispense or not to dispense binder liquid at each of many locations in the printing plane, usually in a grid format.

In another embodiment, more than one binder or dispensed liquid may be involved in order to dispense different substances at different locations. To accomplish this, the independent instructions for each available binder liquid instruct whether to dispense or not to dispense at a particular location. This can further include a check to prevent certain multiple dispensing of binders at given locations. Thus, the machine instructions at each possible printing point are a series of binary (i.e., yes-or-no) instructions for each of the available dispensers.

In some types of printheads it is even possible to vary the amount of liquid dispensed at a given print command by varying the electrical waveform driving the dispenser. The technologies providing capability include piezoelectric printheads and microvalve based printheads. In such a case, additional information would have to be associated with each print command in the machine instruction file.

Thus, in addition to the geometric data, the machine instruction file also contains compositional information relating to the situation where more than one binder substance is dispensed onto the powder.

The above description provides methods of manufacturing biomedical devices such as implants that yield at least superior dimensional matching to the patient's body and hence should promote superior tissue and bone ingrowth as compared to conventional methods. In general, the smaller the gap between fragments or surfaces which are intended to heal to each other, the greater the likelihood of successful healing. The biomedical devices of the present invention are anatomically accurate, thus providing an optimal fit with the patient's anatomy, which should promote healing. Furthermore, internal microarchitectures can be designed into the biomedical device to promote, guide, or discourage ingrowth of bone or other tissue in specific places. The configuration of the architecture provides an environment beneficial to and optimized to cell ingrowth, and further can be designed to create a unique cell-surface interface that facilitates rapid and specific cell migration into the biomedical device. This is possible due to specifically designed architecture as well as the ability to place drugs, gene fragments, comb polymers, and growth factors in specific locations within the biomedical device. Such details are included in the machine instruction file as just described. Using the machine instruction file, the biomedical device is manufactured such as by three-dimensional printing. It is then inspected, sterilized if required, packaged, and delivered to the user.

Figure 3A:
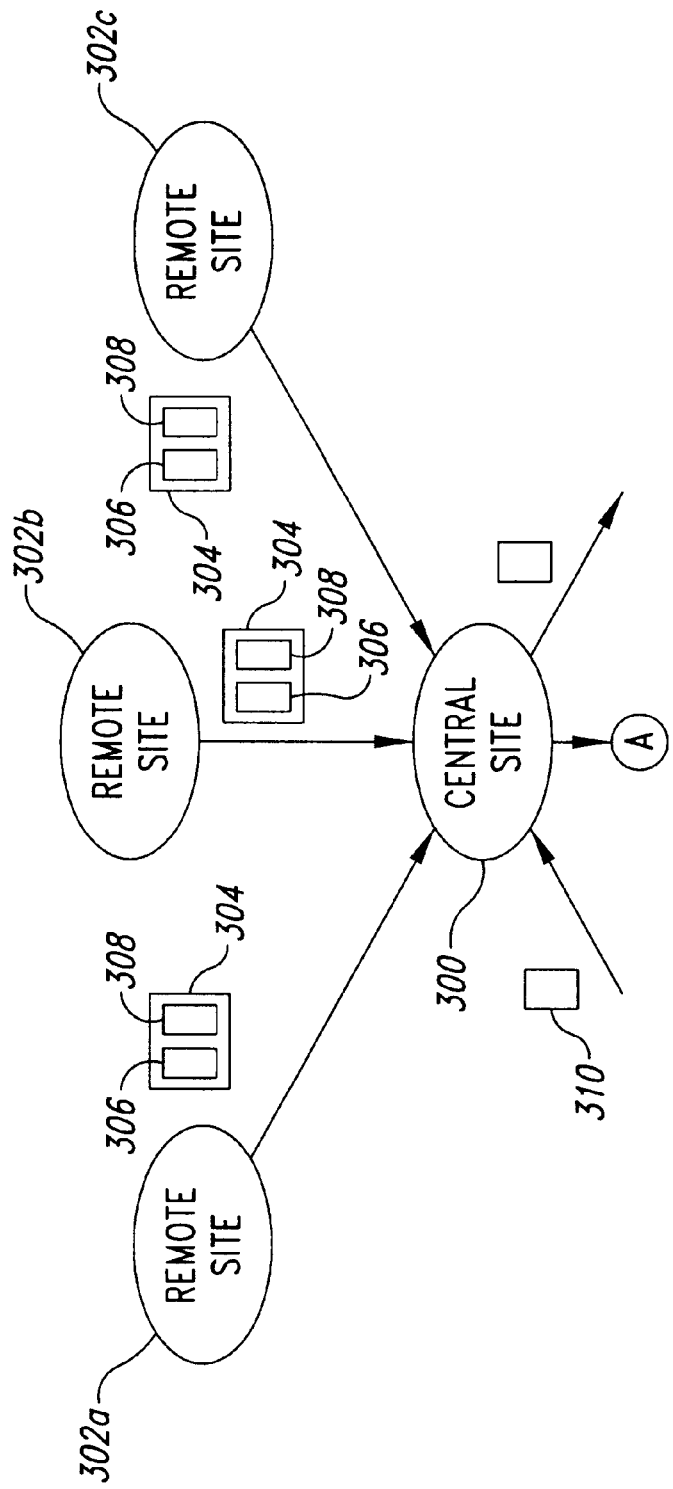
FIGS. 3A and 3B is a schematic diagram showing the flow of data between remote sites and a central site, and showing an alternate embodiment in accordance with the present invention that allows the option of customized manufacture or customized selection of the biomedical device.
Figure 3B:
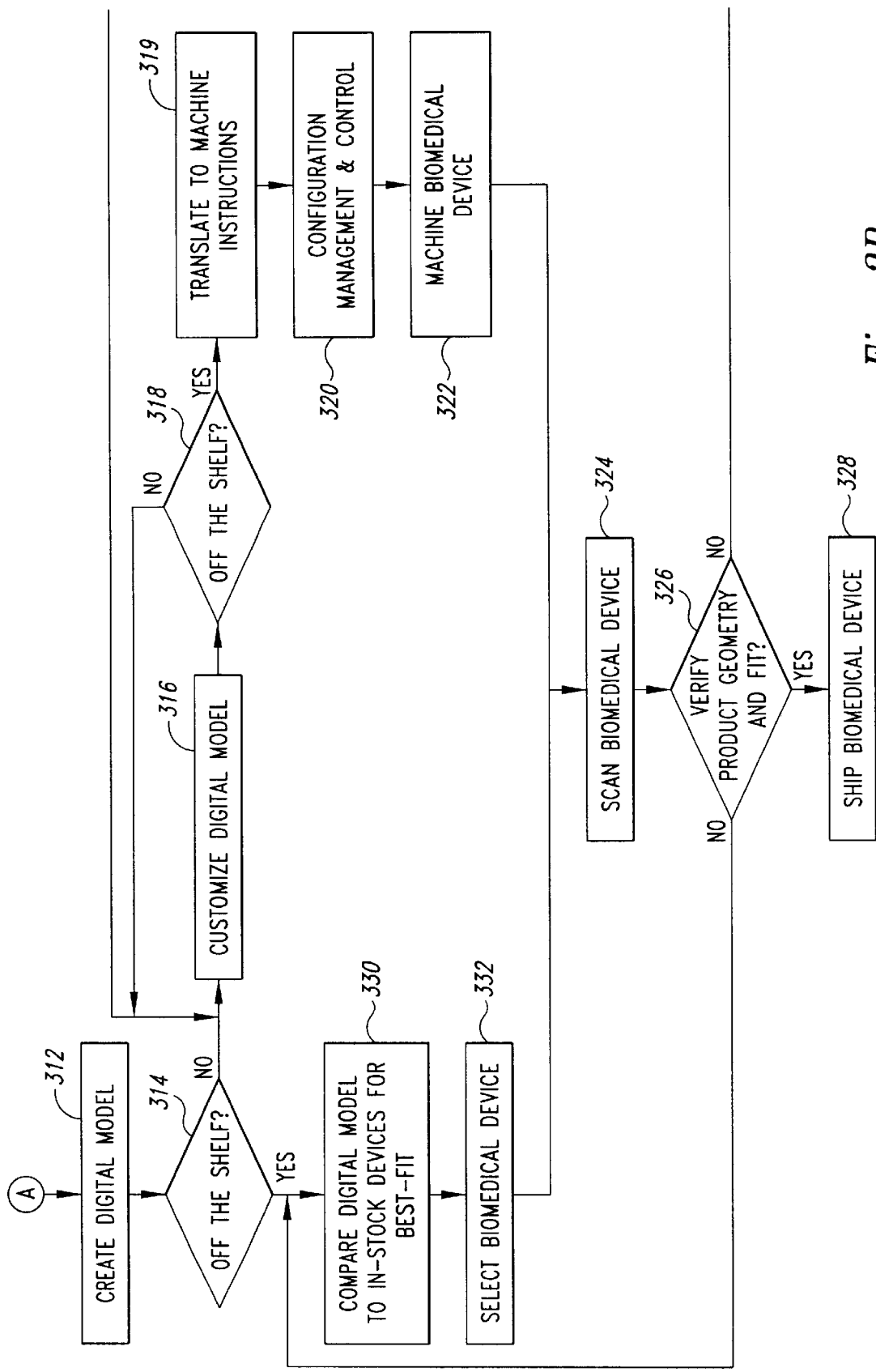

FIGS. 3A and 3B is a schematic diagram further illustrating the flow of data between remote sites and a central site, and showing an alternate embodiment in accordance with the present invention that allows the option of customized manufacture of the biomedical device or customized selection of the biomedical device from a set of pre-designed and possible pre-manufactured biomedical devices on a best fit basis.

A central site 300 receives patient specific data 304 from remote sites 302a, 302b, 302c, processes some of the data 304, interacts with remote sites 302a, 302b, 302c, and is involved in the manufacturing and shipping of parts to remote sites 302a, 302b, 302c. The central site 300 receives and processes patient specific data 304 such as patient information 306 and radiological data 308 such as an MRI or CT scan data. The central site 300 can also receive and process product specifications and product design requirements 310, which are integrated at the central site 300.

Processing of the raw patient data 306 such as the CT/MRI scan data 308 and patient information 306, together with the product specifications 310 involves transmission of data via the Internet, intranet, extranet or other communications network and can involve interaction with the patient and/or physician so as to determine choices of features of the biomedical device such as an implant to be selected or manufactured. In step 312, the central site 300 creates a multi-dimensional digital model 312 of the proposed biomedical device, incorporating additional details or features not included in the radiological data 308, as previously described. The use of network computer communications also permits return transmittal of information from the central location to the doctor/patient at the remote sites 302a, 302b, 302c.

In step 314, the central site 300 determines whether the biomedical device will be custom designed and/or manufactured, or whether the biomedical device will be custom selected from a number of existing designs and/or manufactures. Each approach has unique advantages, as described below in reference to the specific implementations.

Under the custom design and/or manufacturing approach, biomedical device design is performed interactively or collaboratively in nearly real-time by iteratively customizing the digital model, such as shown in step 316. This allows the physician to make suggestions and the CAD operator such as a clinical design engineer, to implement the suggestions, even if the physician is located a great distance away from the CAD operator. The CAD operator can apply specialized knowledge in materials and structures in implementing the suggestions. This collaboration is facilitated by the use of the Internet or similar interactive telecommunication network. Information may be transmitted back to the treating physician showing how a proposed device would fit into the patient's body. Thus, the digital model may include patient tissue and structure surrounding the biomedical device, to assist in visualizing the fit. Although the dimensions of the reconstructive, augmentative, rehabilitative or cosmetic device are probably the most common subject of customization, there are also other parameters which may also be interactively tried and sampled and viewed between physically separated locations, such as material composition of the implant, gradients of properties, porosity, additives, color, and the like. Such visualizations can be returned via the computer network to the physician for evaluation.

Such a system, particularly if it operates in near real-time, could allow a substantial number of design iterations in a short period of time, and could provide the a capability of concurrent design or collaborative or interactive design. In addition to simply indicating the fit and attachment of the reconstructive device, such information may be generally useful in planning surgery, and patient post-operative appearance.

In step 318, the central site determines whether or not the design has been accepted or approved, typically based on a decision by the physician. If not accepted or approved, the central site 300 allows the interactive design process to continue, returning to step 316. If accepted or approved, the central site 300 initiates the manufacture activity. At this point the digital model resulting from the consultative process is translated into manufacturing instructions in step 319, as previously described. The central site 300 executes various configuration management and control operations in step 320, for example, ensuring that sufficient materials are available, ordering replacement materials, and entering the specific biomedical device order into a manufacturing work flow. In step 322, the central site 300 custom manufactures the biomedical device, according to the machine instructions. In step 324, the manufactured biomedical device can be digitized, for example via a laser scanner, mechanical touch probe, or other geometry acquisition device. In step 326, the results compared to the digital model to verify the product geometry and patient fit. If the verification is unsuccessful, control returns to step 316 and the process is repeated. If the verification is successful, the central site 300 ships the biomedical device to the appropriate remote site 302a, 302b, 302c, in step 328.

Under the customized selection of the biomedical device on a best fit basis approach, the digital model is compared to "in-stock" biomedical devices or designs to find a best fit device based on a patient's unique data. In step 330, the digital model is compared to a number of standard designs at the central site 300. In step 332, the one of the standard biomedical devices is selected for the patient on a best fit basis at the central site 300. In step 324, the selected biomedical device is scanned and, in step 326 the results compared to the digital model to verify the product geometry and patient fit. If the verification is unsuccessful, control returns to step 330 and the process is repeated. If the verification is successful, the central site 300 ships the biomedical device to the appropriate remote site 302a, 302b, 302c, in step 326. The selected biomedical device can be shipped directly from stock, if available, or manufactured according to a predefined set of machine instructions.

The steps 332 and/or 326 will typically include receiving approval or agreement from the physician. Upon final agreement, the biomedical device is retrieved from stock, if available, or manufactured to order, but with less specific labor and effort than is involved in a fully customized design. Depending on various factors such as price, timing, and the location in the body, customization can include a best fit from standardized sizes and/or one of a kind customized construction.

There are several differences between a completely customized biomedical device and a best fit from stock biomedical device. A completely customized biomedical device, will likely have the best possible match to a patient's own dimensions. However, only one or a small number of copies would likely be made. Thus, the cost of producing the fully customized digital model is completely borne by one patient or insurer. On the other hand, if a fully customized implant is not necessary, there are two possible approaches. One is to supply a biomedical device that is fully customized for another patient who closely resembles the current patient. The cost could be significantly reduced, although the fit will not be as good. An even lower cost alternative employs a set or series of generic digital models, not necessarily derived from the specific data of any particular patient. The resulting biomedical devices would not fit as well as a customized biomedical device, however these parts could be manufactured simultaneously at lower manufacturing costs than patient specific customized parts.

In three-dimensional printing, there are economics advantages to printing a whole tray or bed full of similar parts in a single run. Thus, if generic parts were being manufactured, it would be preferable to manufacture a substantial number of them simultaneously. This means assembling a machine instruction file in which instructions for the generic part are repeated a number of times. If patient-specific parts are being manufactured, it would also be preferable to manufacture several parts in a single run, which would mean stringing together the individual print instructions for a number of different patients' parts to make one complete set of printing instructions or machine instruction file.

Through the techniques described here, the ability for customization or matching of the reconstructive augmentative rehabilitative or cosmetic device to a patient's individual needs is maximized, as is the amount of information available to the surgeon before the operation, while the time required to produce a better product is minimized.

The present invention's use of an electronic design and manufacturing model also permits additional advantages such as compilation of databases or profiles for individual physicians and/or hospitals or for individual patients, inventory control, record-keeping and billing, product design updates and client feedback, and follow-up notices to users. Such information can be maintained on a secure Web site, available to appropriate categories of users such as through the use of passwords or similar access restrictions.

Figure 4:
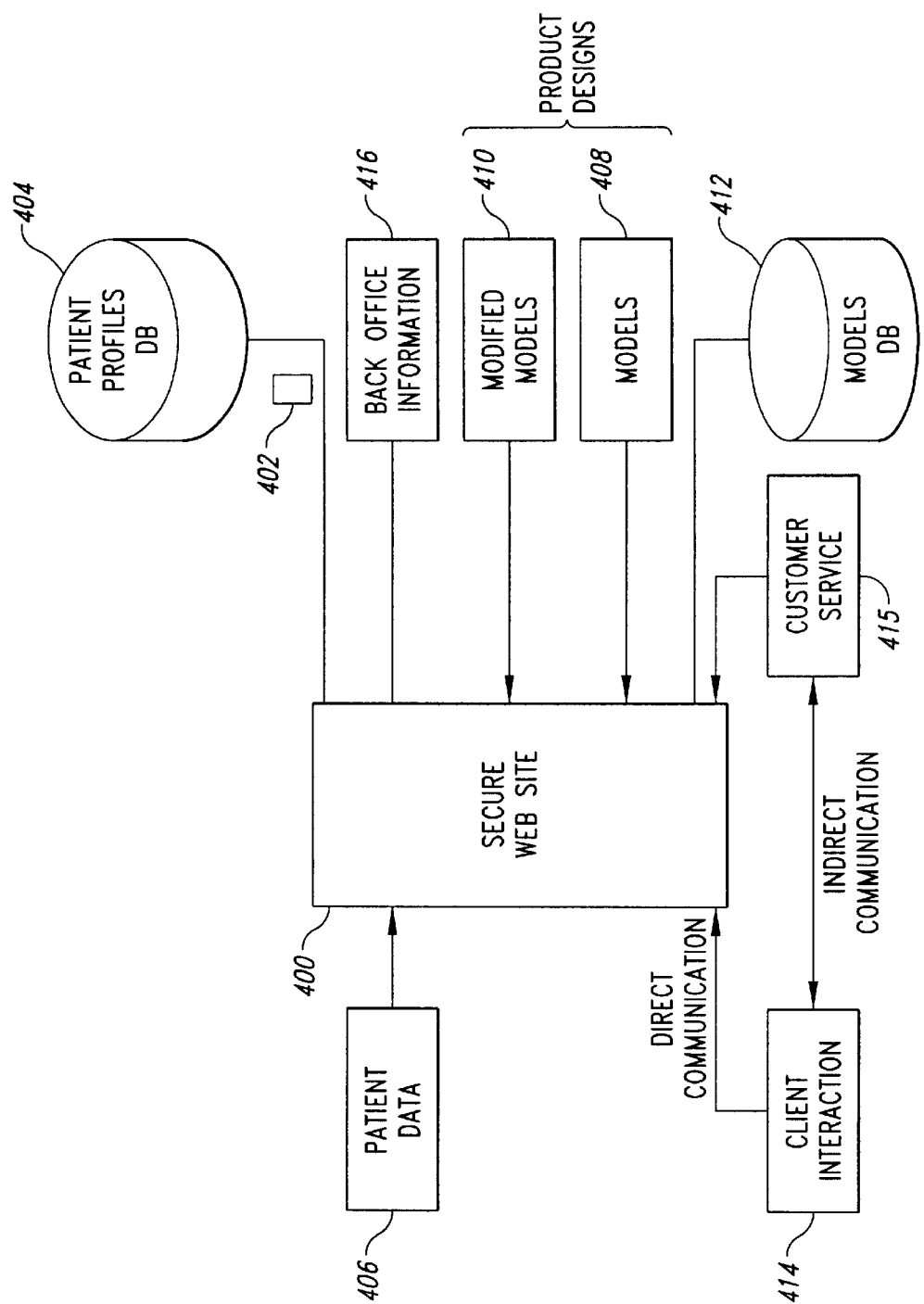
FIG. 4 is a schematic diagram showing a centralized Website to manage data and data interactions with various parties in accordance with an illustrated embodiment of the present invention.

FIG. 4 is a schematic diagram of an exemplary flow of data and other information to a Website 400 for implementing the present invention according to one illustrated embodiment. As discussed above, the Website 400 can be hosted on one or more computers, such as the server computer 18 (FIG. 1). Access to the Website 400 or appropriate portions of the Website for specific users or categories of users can be controlled by passwords or similar methods, including biometric verification. In order to provide for privacy of medical records, encryption, password protection and/or digital certificate authentication could be used for all data transmissions.

As shown in FIG. 4, the secure Web site 400 is created to allow for the management of information and data between clients at one location and designers, engineers and/or manufacturers at another location. Clients may include medical providers such as physicians, oral surgeons, maxillofacial surgeons orthopedic surgeons or other surgeons.

The information and data may be organized as patient profiles 402 stored in a patient profile database 404. The patient profile database 402 may include orders for reconstructive implants, as well as directions and review by the attending physician or surgeon. The patient profile database 402 may also maintain patient records and histories. The secure Web site 400 accepts the input of patient specific data (i.e., radiological data and/or patient information) 406, and facilitates the management of imaging data such as an MRI/CT radiological data. Thus, the secure Web site 400 receives patient data 404, including specific imaging data such as MRI/CT files which provide the basis for developing the customized biomedical devices.

The Web site 400 receives initial digital models 408 and modified digital models 410 from the designers. As discussed above, the initial digital models 408 are develop based on the patient data 406, particular the radiological data. The Web site 400 provides an interface for managing, accessing and displaying the digital models 408, 410 of the biomedical devices such as implants. The digital models are stored in a model database 412. The interface is available to the designers, engineers, manufactures, physicians and surgeons to the degree necessary for each to perform their assigned tasks. The interface may contain separate components or subsets, each accessible by only a subset of users. These components or subsets may take the form of specialized Webpages that are tailored to the unique tasks of each individual based on the individual's assigned role. Thus, the physician will likely interact with a different subset of the interface than the designer or engineer. The separate components or subsets also provide a way to limit access to information based on assigned role. Thus, for example, it is possible to not only deny access to information, but to even prevent a user from determining that such information exists, since a particular component or subset may omit any icons associated with a particular piece of information.

The Web site 400 also provides an interface for receiving and managing client interaction 414. Client interaction 414 may take the form of an initial proposal for the design of a product for a patient. The Web site 400 may also receive client interaction 414 in the form of an initial patient profile, a review of the proposed product, comments and questions regarding the product, and an approval of the final order. Client interaction 414 can take place directly through the Web site 400, for example electronically via http requests or email. Additionally, or alternatively, the client interaction 414 can take place indirectly through communications with customer service personnel 415, for example telephonically, electronically via email, in-person, or through traditional mail routes.

Customer service 415 responds to inquiries regarding customized biomedical devices as well as matching product designs to patient data 406, and generally facilitating the ordering process. Customer service 415 also may provide electronic mail updates or alerts regarding the biomedical devices, may respond to client's queries via telephone, mail, or electronic mail, and may facilitate direct sales.

The Website 400 receives back office information 416 from internal company information systems. The back office information 416 allows the Website 400 to control implant data, maintain order status through delivery, control inventory, perform Web management, and perform billing. As is illustrated by the above discussion, the secure Web site 400 provides a central information exchange platform.

As discussed above, the client can view the final product design as embodied in a digital model 410 via the a component or subset of the secure Web site 400 prior to manufacture and/or shipment. Records and files can be stored as back office information 416 in the internal information systems for future reference. The secure Web site 400 may also allow the client to directly input specifications, requests, or parameters or requests such as requests for modifications. The Website 400 can maintain a permanent record of the physician's instructions in ordering the part.

A secure central Website 400 can be used for comparing data taken on a given patient at different times, to obtain specific dimensional comparisons or changes. In taking a CT scan or a MRI scan, data is taken at a series of imaginary planes through a patient's body, with the planes typically being spaced from each other by a distance of 1 to 2 mm. For two different scans taken a substantial amount of time apart from each other, the positioning of the patient is likely not the same each time, and even if it were, the position of the imaginary planes at which scans are taken would not be the same. Thus, to obtain detailed dimensional data, it is useful to transform the raw CT or MRI data to a digital model. A digital model involves defining boundaries such as between soft tissue and bone, by defining the edges of bone, and then in all dimensions fitting curves to define the surfaces of the bone throughout space. These boundaries are not inherent in the radiological data, and thus must be added in creating the multi-dimensional digital model.

Furthermore, for comparing dimensions of such data taken from the same patient at different times, it is advantageous to use the digital model processed from the raw CT or MRI data, because the digital model contains the detailed calculated positions of curved surfaces throughout space, rather than just at locations at which scans were actually taken. Once the position of a given body part in one digital model is suitably related to the position of the same body part in a digital model from a scan at a different time, differences in dimensions can be calculated, and increments of recession or growth can be calculated. This matching could be done as previously described by calculating centroids and matching their position, together with orientating the two models so that the mathematical or Boolean difference, namely, volumes belonging to one or the other model but not both, is minimized.

Comparing two different digital models may provide evidence of reabsorption or deterioration of bone indicating need for intervention, or evidence of normal growth, or evidence of ingrowth as a way of monitoring recovery after surgery. In the case of an implant made of reabsorbable material, this may provide a way of monitoring the extent of reabsorption. It may also be useful, as described earlier, to compare MRI and CT scans taken from the same patient, at either the same or different times. Having the facility of a central Website 400 (FIG. 4) makes this easier and provides a capability which might not be available at every physician's office.

Dimensions may not be the only parameter that can be usefully compared between digital models or raw data taken at different times. Bone density might be able to be compared as an indicator, for example, of osteoporosis or other degenerative condition. Even local chemical composition, which is one of the strengths of MRI as a diagnostic technique, might be able to be compared or analyzed. Having all of this maintained on a central site, which may include specialized software, enables time-variation or progression to be studied which may include various stages in the progression of a degenerative disease, followed by design of a custom implant, followed by noting the appearance after implantation of the custom implant, followed by monitoring any changes in nearby bone after implantation, and even including indication of how much reabsorption has taken place in the case of a reabsorbable implant.

The computer facilities for creating multi-dimensional digital models from individual CT or MRI scans may not exist in every physician's office, and similarly the computer facilities for comparing two different digital models and detecting small dimensional changes are even less likely to exist in every physician's office. Thus, the use of telecommunication such as the Internet provides the availability of such services to any location having appropriate communication facilities, regardless of geographic location.

In the case of an implantable drug delivery device, measuring the remaining size of the implantable drug delivery device could provide indication of how much drug has been delivered so far. In all cases, it would be desirable for communication with the central Website or facility to be encrypted, password protected and/or authenticated using digital certificates as mentioned earlier and as is known in the art.

In some instances, the present invention may be used in a way which does not involve manufacturing to order, but rather involves selecting the best fit from a stock of already-manufactured components or designs. While selection from stock does not provide all of the advantages of manufacturing completely customized parts to order, it nevertheless would provide some degree of customization that might be adequate for certain purposes. It also would be even faster than fully customized manufacture. In this sort of application, the central Website 400 would still receive radiographic data pertaining to a specific patient, and could assist in deciding which stock item should be used. The selected stock item are shipped to the physician. The central Website 400 would have further usefulness in that it could be used for maintaining records of inventory, records of rates of use, and could indicate the need for replenishing items which are out of stock or nearly out of stock. Of course, similarly, for custom manufacturing, the Website 400 could still help to maintain inventories of predict usage patterns and inventories of raw materials.

One application of the present invention includes the providing of reconstructive or cosmetic implants to augment the bony material of the human jaw. In the United States there are approximately 20 million people who have lost all the teeth from at least one jaw. There are also other people who have lost many individual teeth. When all or many teeth are missing, especially from the lower jaw, the bone gradually disappears by reabsorbing back into the body because of lack of mechanical stimulation or for other reasons. Eventually this affects the facial appearance. Buildup of the jaw with replacement bone from the same person (autograft) or from cadavers (allograft) can remedy this problem but typically this is only a temporary solution because over several years the grafted bone reabsorbs for the same reasons that the original bone reabsorbed.

One solution is to implant a custom-shaped piece of artificial bone at least part of which is made of a material that is not reabsorbable. For example, current work on an alveolar ridge replacement focuses on using hydroxyapatite powder as the basic material. Hydroxiapatite is not reabsorbable into the human body. An example of a binder that may be dispensed onto hydroxyapatite powder to build parts is an aqueous solution of polyacrylic acid (PAA). Following dispensing of the binder, the "green" (uncured) ceramic part is heated to decompose the binder and then heated to a higher temperature to cause sintering thus fusing particles together. The porous sintered ceramic may then be infused with a polymer to further enhance its mechanical strength, such as polymethylmethacrylate (PMMA). Such parts may then be surgically installed in the jaws of patients.

For completely edentulous patients it is possible that a variety of standard sizes may suffice, but it is also possible that parts manufactured from patient-specific data may be preferable. For partially edentulous patients, each with their own pattern of missing teeth, there may be more need for patient-specific manufacturing. In all of these cases, the use of a computer network to transmit patient-specific data is valuable, as is the use of the computer network to transmit patient-specific data such as visualizations back from the central location to the patient location.

The alveolar ridge is not the only body part for which it may be useful to manufacture replacement pieces of possibly custom-shaped bone-like material possibly including Internet transfer of data to provide exceptionally fast response and delivery time. Other possible body parts, shapes and devices include: cranial plugs; cheeks; mandible onlay; mandible extension; chin; nose; dental plug; external ear; gauze; orbital implants; orbital floor; orbital wall; orbital rims; orbital socket; croutons; wedges; plates; sheets; blocks; dowels; spine cage inserts; screws; tacks; custom pieces; cartilage; and soft tissue. These body parts are not meant as a complete or limiting list; others are also possible.

The term "croutons" refers to pieces of bone-like material used during surgery to fill voids in bone such as in piecing together complex fractures, to improve the likelihood of successful healing. They serve as building blocks. Their shapes may be standard or custom or a hybrid and they may or may not include features for attachment. Wedges, sheets, plates, blocks and dowels are basic shapes similar to croutons. Orbital implants, rims, sockets, floors and walls are portions of the bone near the eye. Dental plugs are small pieces of bone substitute that could be placed at the site of a tooth extraction. A cranial plug would be used to fill a hole made in the skull for surgical purposes.

Some of these such as the external ear, and perhaps the nose, are non-rigid and would be made out of silicone or polyethylene, but again these are merely examples and other materials are also possible. For devices that are desired to be reabsorbable into the human body, examples of suitable materials are poly-L-lactic acid (PLLA) and poly-lactic-co-glycolic acid (PLGA), and similar polyesters. Suitable printing techniques take advantage of the solubility of these materials in chloroform.

Implantable drug delivery devices contain drugs and are made of a material that slowly degrades or dissolves in the body. Their function is to release drug gradually as they dissolve. The time scale of drug release is typically of the order of months, perhaps many months. Implantable drug delivery devices would typically be implanted by a relatively minor implantation procedure.

Another type of manufacturable device are surgical leave-behinds that might contain and release drugs. A surgical leave-behind is placed in a patient's body as a surgical incision is being closed, with the intention that it release drugs as it dissolves. Surgical leave-behinds are essentially a form of implantable drug delivery devices, which is implanted during a surgical procedure that is performed primarily for other reasons. Their designed release period is determined by the time scale of processes that take place during wound healing and recovery from surgery and is typically measured in days.

Categories of drugs that might likely be packaged in surgical leave-behinds include local anesthetics, anticoagulants, antibiotics, chemotherapeutic or other anti-cancer drugs, anti-nausea drugs, growth factors, hormones or similar substances to promote healing, and the like. Both implantable drug delivery devices and surgical leave-behinds could quickly be made-to-order, with unique specification of geometry, content of drug or drugs, dosage, dissolution time, or any other design variable, in part through the use of the internet, using the methods described herein.

The method of the present invention can also be used to quickly generate and deliver tissue scaffolds of customized shape, composition, and the like. A tissue scaffold is a device having some porosity or internal voids which are designed so that cells tend to grow into them. In some instances cells are seeded into the scaffold in advance of when the device is to be implanted in a person's body, and are allowed to grow for a period of time in an environment conducive to their growth, such as a bioreactor. Often the scaffold is designed to dissolve or be absorbed by the body or the surrounding medium over a certain period of time, which provides further spaces into which cells may grow.

The geometry or architecture of a tissue scaffold has a significant effect on how well cells grow into it. The overall dimensions and geometry of the scaffold may be something that needs to be designed for the dimensions of an individual patient, or other features of it may need to be customized for an individual patient. Other features of the design of a tissue scaffold which may affect its success in growing cells include composition of bulk materials and surfaces, deposition in specific places of surface-active agents which may either increase or decrease hydrophobicity, and deposition in specific places of bioactive materials, such as growth factors, and peptides. Use of the Internet for data transmission, possibly including patient-specific data, together with use of the rest of the techniques disclosed herein, can significantly speed up the availability time of custom-made or patient-specific tissue scaffolds.

In another embodiment, the present invention provides a new method of rapid design and manufacture of custom pharmaceuticals drugs such as Oral Dosage Forms (ODF) (pills), short-run applications to meet small, acute or emergency needs via transmission of data over computer networks. In general the process would be what has already been described but simpler in that it would not require transmission of any detailed graphical data either from or to a physician. Today most simple pills of common pharmaceuticals are of constant composition throughout and are made by pressing powder into a tablet shape.

There is a need to design and manufacture more complicated geometries of pills which would provide for delayed or gradual release of active pharmaceuticals, sequenced release of more than one pharmaceutical in a single pill, and in general somewhat arbitrary release profiles of multiple active pharmaceutical ingredients, all governed by the geometric design of the pill and the dissolution behavior of appropriate portions of the pill in bodily digestive fluids. For example, the ability to combine multiple pharmaceutical compounds in a single oral dosage form may be a way of improving patient compliance and accuracy in following instructions for self-administering medications. In general, noncompliance is a significant source of error or failure. Noncompliance can include patient unwillingness to take drugs, and also patient error in taking drugs. Compliance of patients would be increased by anything that decreases the number of pills that must be taken and/or decreases the number of times per day that pills must be taken. This may be useful, for example, in connection with treating either elderly or very young patients. For example, it may be desirable to combine, in one oral dosage form, a first medication with another medication to counteract side effects of the first medication (e.g., nausea).

There may further be reason for one drug or medication to be time-delayed with respect to the other drug or medication. There may be so many possible combinations of drugs that it is not practical to pre-manufacture very many combinations of them, and yet with Internet-enabled communications and rapid manufacturing techniques, such customization and made-to-order pills would be practical. This would also enable doctors to adjust doses based on patient response or patient-unique factors, including individually adjusting doses of each of multiple medications contained within an Oral Dosage Form. This resembles trends in other manufacturing industries, even for products as complicated as automobiles, to cut inventories and to offer more individualized and yet still rapid response to customer needs by manufacturing-to-order. The use of the Internet helps to enable such a system to offer several-day or even faster turnaround, a convenience that can significantly change the way in which pills are made and delivered to patients.

The manufacturing of the ODF can be done by three dimensional printing, layering of premade sheets, or some combination of the these or related techniques. The present invention allows the prescribing physician to transmit the desired prescription for specified active pharmaceutical ingredient(s), dosages, and customized release profile and/or sequence via a computer network, such as the Internet, to a manufacturing location, and have pills manufactured to order with the prescribed quantity and release profile of active pharmaceutical ingredients. These customized pharmaceuticals can then be delivered directly to the patient. Again, the use of computer networks means that even if only a few manufacturing locations exist, it is possible for these products to be delivered to patients quickly, in a cost effective manner, and with minimal geographic limitations.

Additionally, a secure Web site can serve many related functions relating to record keeping of a patient's usage of pharmaceuticals, recording the issuance of prescriptions from physicians, checking for interactions with other drugs which the patient may be taking, refilling a prescription or limiting the number of refills of a prescription, and sending follow-up notices to either the physician or the patient. Billing can also be accomplished through such a Web site, and interaction between the physician, patient, and insurance company can be facilitated. Product design updates, client feedback and follow-up notices to users can also be accomplished through such a Web site, as can generation of statistical data. This method can include transmittal of information back to the prescriber at the time of prescribing, before finalizing of the order, or later. Such information can be maintained on a secure Web site that is made available to appropriate categories of users, possibly including the use of encryption, passwords, and/or digital certificates.

In addition to implants, which would be defined as objects which are totally enclosed inside the body when they are put into use, the same techniques could also be used for manufacturing tooth substitutes or parts of teeth via communication of dimensional information to a distant site for manufacture. This could be done either in conjunction with reconstruction of maxillofacial bone products as already described, or separately. In the case of separately, it could be used to fabricate objects, e.g., dental implants, dental onlays, dental inlays, dental crowns, dental caps, etc., i.e., objects which are not at all enclosed by the skin of the body and which are visible when installed.

A practical example of one procedure for generating implant models from CT or MRI data, follows. Other implementations are of course possible.

Initially, the original medical imaging data is collected from the patient by the radiologist or surgeon using commercially available scanning devices. For example, the radiologist or surgeon may employ commercially available CT and MRI scanning devices. CT and MRI scans are arrays of two-dimensional images that each represent a specific scanning slice through the patient. Resolution of images as well as the slice thickness is determined by the physician or radiologist and is a function of radiation dosage to the subject, size of the region to be scanned and required scan resolution.

Figure 5:
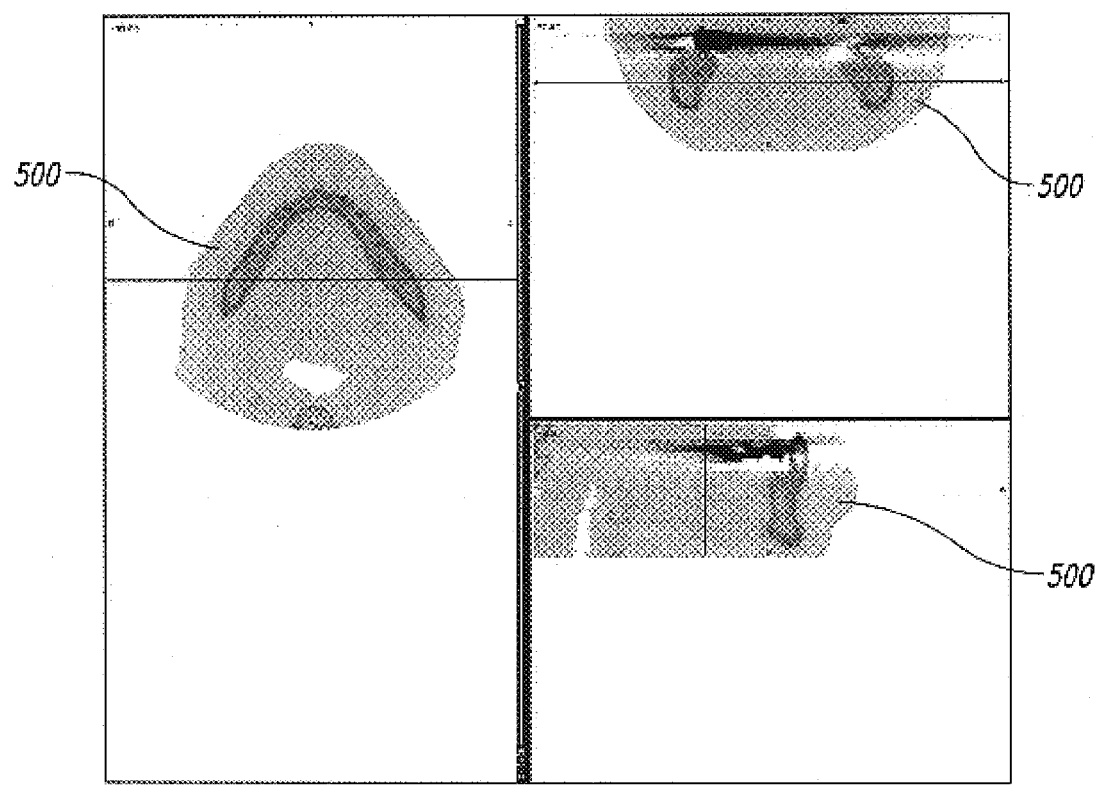
FIG. 5 is a computer screen print of three views of a gray scale image of anatomical data, showing a mandible as captured by a CT or MRI imaging device.

As shown in the three views illustrated in FIG. 5, the anatomical data 500 is then imported into Materialise MIMICS software. Each slice is represented by variations in the gray scale of the image. The contrasts of the images are adjusted to aid in the separation of bone from soft tissue by establishing appropriate threshold values. Working layer by layer, the anatomical regions of interest are isolated.

Figure 6:
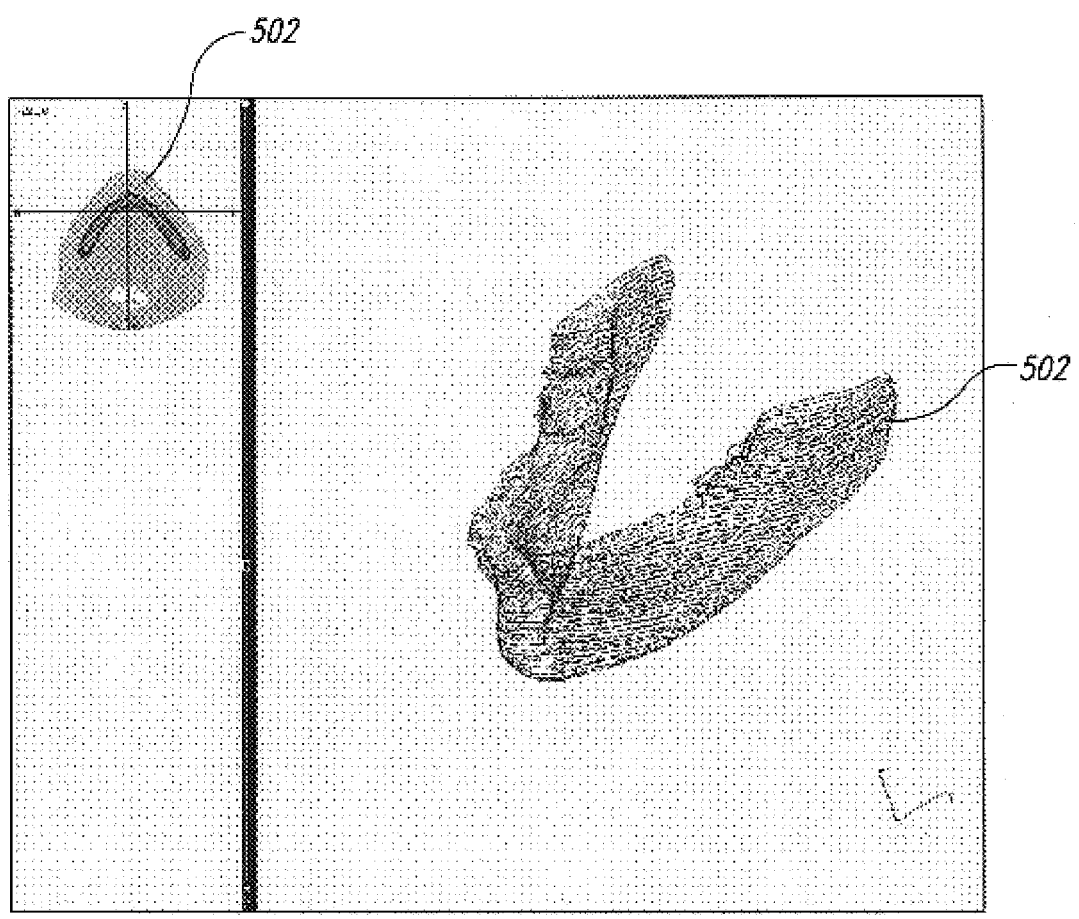
FIG. 6 is a computer screen print of a three dimensional volume module of the mandible of FIG. 5.
Figure 7:
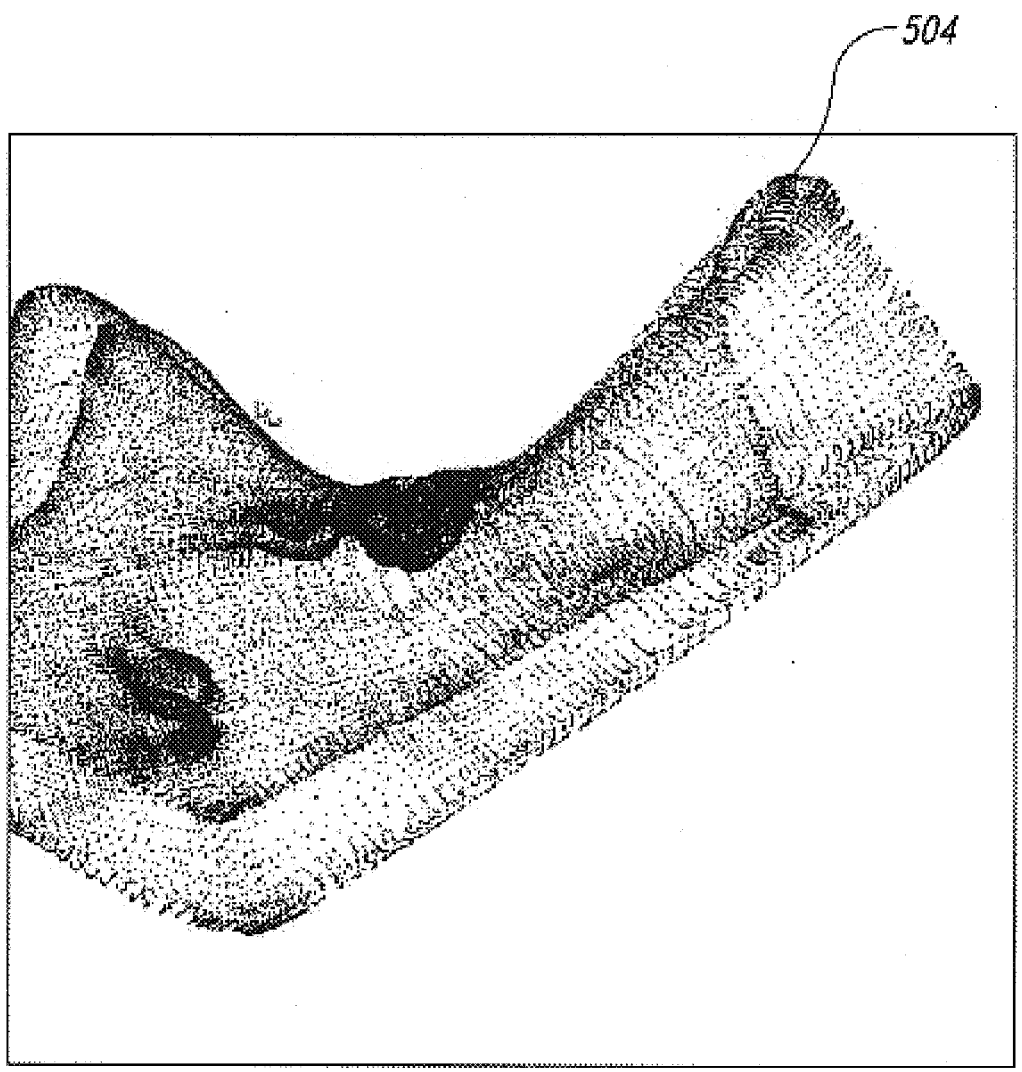
FIG. 7 is a computer screen print of a point cloud file of the three dimensional volume module of FIG. 6.

Once the layers have been segmented, the software allows for inter-plane linear interpolation or cubic spline convolution calculations in order to decrease the slice thickness of the data set. As shown in FIG. 6, a three-dimensional volume model 502 of the anatomical data results. From there the data can be output as either a Stereolithography Interface Format ("STL") file or as a point cloud file 504, as shown in FIG. 7.

Figure 8:
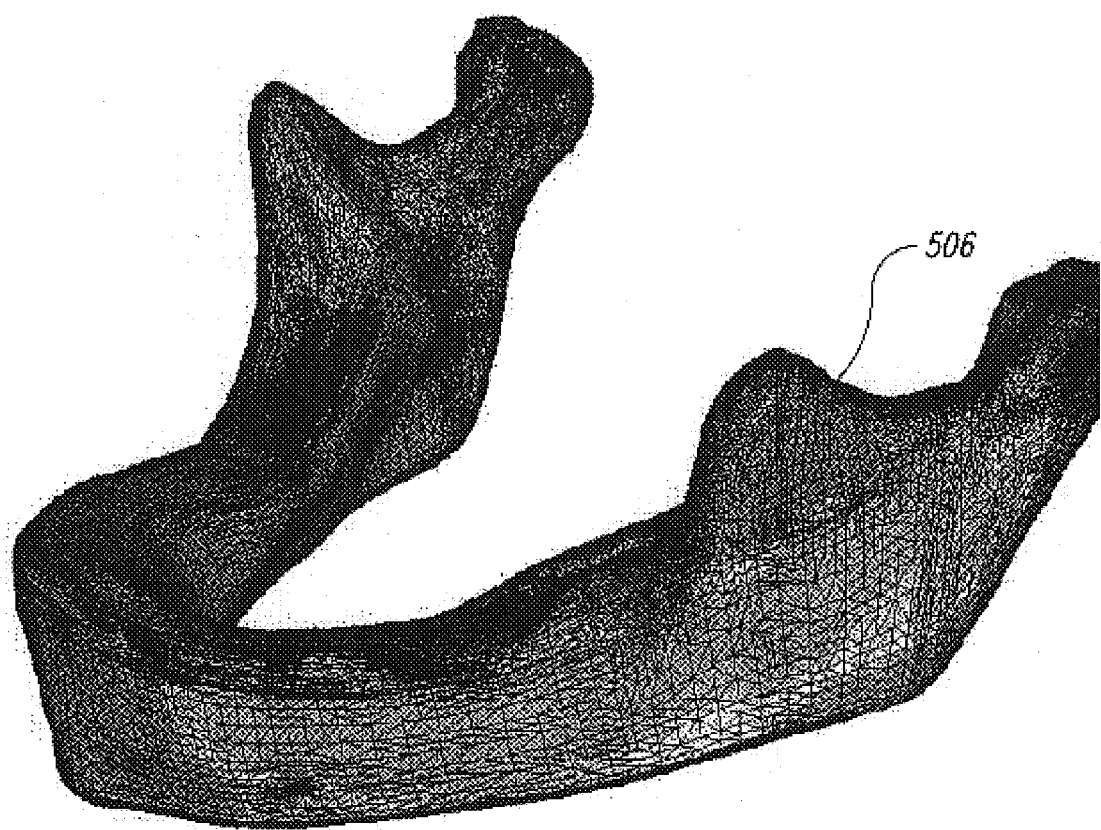
FIG. 8 is a computer screen print of a smooth mesh representation of the three dimensional volume module of the mandible of FIG. 6.

Using the STL file format, the Paraform software can be used to smooth the surfaces of the model. STL files appear as mesh, often forming sharp points. The software allows the user to sculpt and smooth the mesh. When completed, lines are drawn and formed onto the mesh 506, as shown in FIG. 8. (In this case the teeth from the scan were removed to reveal the underlying alveolar ridge.) These lines become the borders of surfaces that will be formed onto the mesh. All of these steps allow the user to control the level of detail of each surface. Once all of the surfaces are joined together forming a "water tight" body, the geometry can now be made into a solid and then exported to the CAD software for further manipulation, for example as a Parasolid file.

Figure 9:
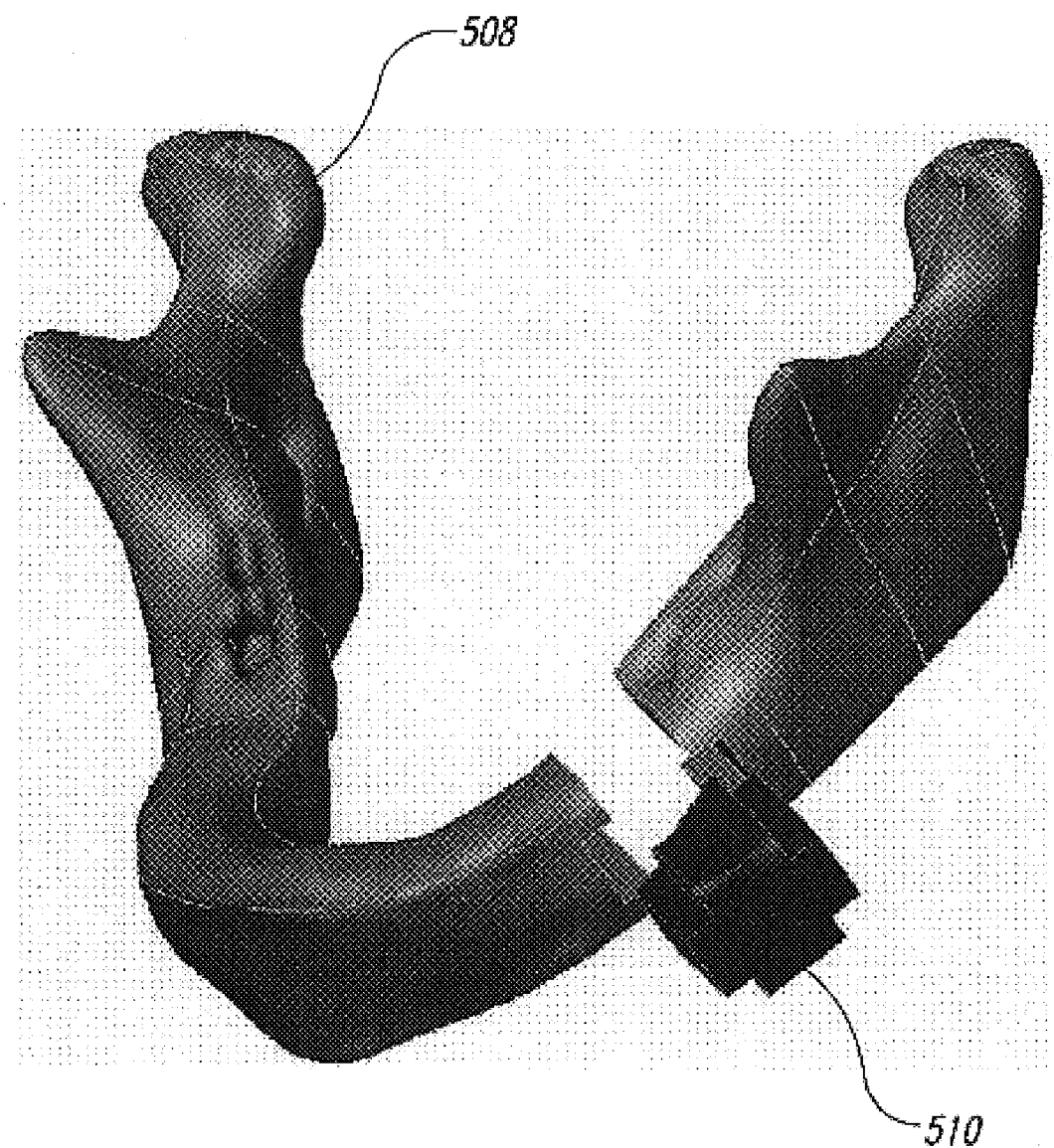
FIG. 9 is a computer screen print of an isometric view of a solid model created from the smooth mesh representation of the mandible of FIG. 8, with a replace portion of the mandible shown removed from the remainder of the mandible.

The CAD software allows dimensional control of features. Prior to this point, the data was similar to clay being formed into the proper shape. Here, each feature (cut, protrusion, etc.) has a defined size and shape. Using physical markers, the geometry can be accurately defined or modified per the required specifications. The mandible 508 shown in FIG. 9, was imported into SolidWorks and a section 510 was extracted to simulate an osseous reconstruction which replaced a tumor or other defect.

Figure 10:
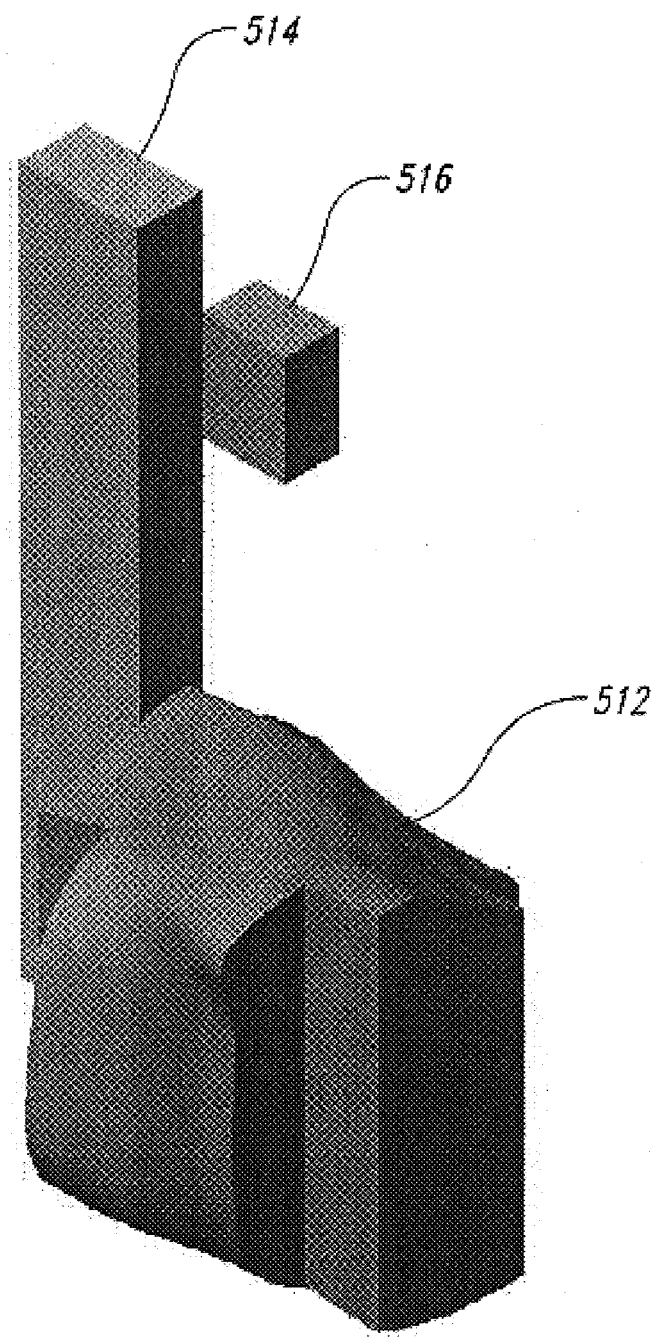
FIG. 10 is a computer screen print of an isometric view of a solid model of three parts including the replacement portion of the mandible and two blocks used in testing.

The parts that are to be fabricated are assembled together within SolidWorks. As shown in FIG. 10, each individual part or subassembly are placed and oriented within an assembly. This is the orientation that will be printed. In the illustrated example, the mandible section 512 is assembled with two other blocks 514, 516 that are typically used for mechanical testing. The assembly is then scanned using a Therics ray casting application that is an add-on module to SolidWorks. The operator specifies the increments and starting positions along the X and Z axes. These represent, respectively, the spacing between scan lines or line spacing, and the layer thickness to slice the model. For each unique combination of X and Z increment values, a ray is cast through the assembly and surface intersection points are captured.

Upon completion of the ray casting, a file is output, shown in FIGS. 11A and 11B, that uniquely identifies the scanned assembly, the scan parameters, and the set of intersection points that were identified. The following example demonstrates a scan of the assembly previously discussed including mandible section and two test blocks. The header information for the ray casting output is bolded in the example file. It includes such information as the assembly file name, save date, operator, date/time of scan, a list of the bodies in the assembly, and the scan parameters used. The actual intersection points encountered during the scanning process include the Cartesian point of intersection, the normal values of the intersection point, the body intersected, and the type of intersection. The most common type of intersection of a ray with a surface is when a ray enters and exits the surface, producing FACE ENTER and FACE EXIT intersection points. These points are used in generating the print job. The ray casting function also detects intersections with edges, vertices and tangencies. These additional types of intersection may prove useful in the future for optimization of the scanning process.

The output file from the ray casting utility is imported into an application to generate a print job for fabrication. The surface intersection points that share the same Z value and intersected part are paired into series of rasters. After determining the model of target machine and printhead configuration that will be used, a series of machine instructions are generated that instruct the target machine on how to coordinate its motions and print patterning. An exemplary set of instructions are illustrated in FIGS. 12A and 12B, where the instructions "F" and "G" are grouped together to represent forward and reverse passes of the printhead. When these instructions are interspersed with the "P" instruction that determines which valves of the printhead are active, printing sweeps are formed. Every print job will consist of interspersed layer spread commands, represented by the "M" instruction, and a series of sweeps. Each layer spread and series of sweeps will reproduce one slice or layer of the parts during fabrication.

Figure 13:
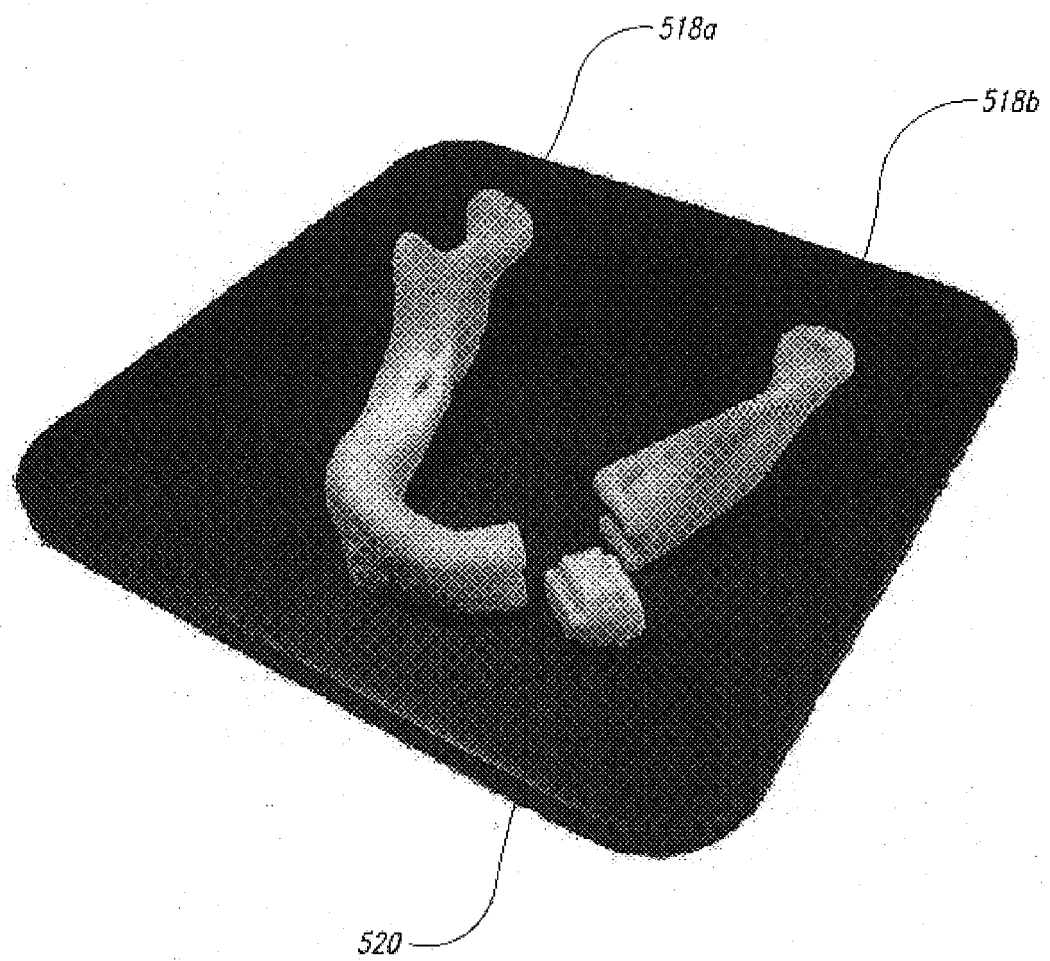
FIG. 13 is an isometric view of three physical components created according to the instructions of FIG. 12.

To perform a fabrication, a print job must be loaded into the Process Control Software on the target machine. Once loaded, the print job may be executed multiple times to generate the required quantity of parts. FIG. 13, shows the three fabricated components 518a, 518b, 520 of the mandible that has been discussed in reference to the above example. The mandible section is fabricated separately from the two larger mandible sections.

Although specific embodiments of and examples for the machine tool system and method are described herein for illustrative purposes, various equipment modifications can be made without departing from the spirit and scope of the invention, as will be recognized by those skilled in the relevant art. The teachings provided herein of the invention can be applied to other machine tools, not necessarily the 3 dimensional printer discussed above. Additionally, the system can employ other computing hardware and network topologies. For example, the client side may include a server for providing network servers to one or more client computing systems. The client and/or server side computing systems may include firewalls where appropriate, to provide enhanced security.

From the foregoing it will be appreciated that, although specific embodiments of the invention have been described herein for purposes of illustration, various modifications may be made without deviating from the spirit and scope of the invention. For example, while generally discussed in terms of solid models, many embodiments can employ other CAD representations including surface modeling and/or wire-frame modeling.

The various embodiments described above can be combined to provide further embodiments. All of the above U.S. patents, patent applications and publications referred to in this specification are each incorporated herein by reference in their entirety. Aspects of the invention can be modified, if necessary, to employ systems, circuits and concepts of the various patents, applications and publications to provide yet further embodiments of the invention. Many of the methods described above may omit some of the described steps, include additional steps, and/or perform some or all of the steps in a different order.

These and other changes can be made to the invention in light of the above detailed description. In general, in the following claims, the terms used should not be construed to limit the invention so that specific embodiments disclosed in the specification and claims, but should be construed to include all biomedical device design and manufacturing machine methods and apparatus that operate in accordance with the claims. Accordingly, the invention is not limited by the disclosure, but instead its scope is to be determined entirely by the following claims.

What is claimed is:

1. A method for customized design of anatomically correct implants for a patient, comprising:

receiving radiological data representing a physical structure of an anatomical body part that is to be replaced, repaired or augmented;

creating a multi-dimensional digital model of at least a portion of the anatomical body part based on the received radiological data; and modifying the multi-dimensional digital model to create at least a first successive multi-dimensional model wherein modifying the multi-dimensional digital model includes adjusting a material density gradation through at least a portion of the multi-dimensional digital model based on a representative material density gradation of similar anatomical body parts, and wherein the first successive multi-dimensional model represents at least one physical characteristic of the anatomical body part not represented in the radiological data.

2. A method employing a computer system for customized design of biomedical devices, comprising:

receiving radiological data representing a physical structure of an anatomical body part;

producing a multi-dimensional digital model of at least a portion of the anatomical body part based on the received radiological data;

securely transmitting the multi-dimensional digital model over a communications channel;

receiving at least one request to modify at least a portion of the multi-dimensional digital model of the anatomical body part;

modifying the multi-dimensional digital model of the anatomical body part in response to the received request;

receiving an approval of the multi-dimensional digital model;

producing a biomedical device based on the approved multi-dimensional digital model, the biomedical device having at least some physical characteristics corresponding to the multi-dimensional digital model;

digitizing the biomedical device; and comparing the digitized biomedical device with the multi-dimensional digital model to verify fit.

3. A method employing a computer system for customized design of biomedical devices, comprising:

receiving radiological data representing a physical structure of an anatomical body part;

producing a multi-dimensional digital model of at least a portion of the anatomical body part based on the received radiological data;

securely transmitting the multi-dimensional digital model over a communications channel;

receiving at least one request to modify at least a portion of the multi-dimensional digital model of the anatomical body part;

modifying the multi-dimensional digital model of the anatomical body part in response to the received request wherein modifying the multi-dimensional digital model includes:

determining a set of engineering constraints on the requested modification; and applying a set of changes within the determined engineering constraints to the multi-dimensional digital model; and receiving an approval of the multi-dimensional digital model.

4. A method employing a computer system for customized design of biomedical devices, comprising:

receiving radiological data representing a physical structure of an anatomical body part;

producing a multi-dimensional digital model of at least a portion of the anatomical body part based on the received radiological data;

securely transmitting the multi-dimensional digital model over a communications channel;

receiving at least one request to modify at least a portion of the multi-dimensional digital model of the anatomical body part;

modifying the multi-dimensional digital model of the anatomical body part in response to the received request;

receiving an approval of the multi-dimensional digital model;

selecting one of a number of already-manufactured biomedical devices on a best fit basis;

digitizing the selected biomedical device; and comparing the digitized biomedical device with the multi-dimensional digital model to verify fit.

5. A server side computing system for biomedical device delivery, comprising:

means for receiving radiological data over a secure communications channel;

means for creating a multi-dimensional digital model based on the received radiological data;

means for modifying the multi-dimensional digital model to incorporate structure not available in the radiological data, comprising:

automated means for selecting an appropriate modification based on received patient related information; and automated means for applying the selected appropriate modification to the multi-dimensional digital model; and means for providing biomedical devices based on the multi-dimensional digital model.

* * * * *